US00RE47740E

(19) United States
(12) Reissued Patent
Maeda et al.

(10) Patent Number: US RE47,740 E
(45) Date of Reissued Patent: Nov. 26, 2019

(54) AMINOPYRIDINECARBOXAMIDES AS CXCR2 MODULATORS

(71) Applicant: Syntrix Biosystems Inc., Auburn, WA (US)

(72) Inventors: Dean Y. Maeda, Seattle, WA (US); John A. Zebala, Issaquah, WA (US); Aaron D. Schuler, Auburn, WA (US)

(73) Assignee: Syntrix Biosystems Inc., Auburn, WA (US)

(21) Appl. No.: 15/210,803

(22) Filed: Jul. 14, 2016

Related U.S. Patent Documents

Reissue of:
(64) Patent No.: 8,779,149
Issued: Jul. 15, 2014
Appl. No.: 13/215,014
Filed: Aug. 22, 2011

U.S. Applications:
(60) Provisional application No. 61/376,224, filed on Aug. 23, 2010.

(51) Int. Cl.

| | |
|---|---|
| ***A61K 31/44*** | (2006.01) |
| ***C07D 401/00*** | (2006.01) |
| ***A61K 31/69*** | (2006.01) |
| ***C07D 211/72*** | (2006.01) |
| ***C07F 5/04*** | (2006.01) |
| ***C07F 5/02*** | (2006.01) |
| ***C07D 239/47*** | (2006.01) |
| ***C07D 401/12*** | (2006.01) |
| ***C07D 413/12*** | (2006.01) |
| ***C07D 213/82*** | (2006.01) |

(52) U.S. Cl.
CPC ..... *C07F 5/04* (2013.01); *A61K 31/44* (2013.01); *A61K 31/69* (2013.01); *C07D 213/82* (2013.01); *C07D 239/47* (2013.01); *C07D 401/12* (2013.01); *C07D 413/12* (2013.01); *C07F 5/025* (2013.01); *Y02A 50/402* (2018.01); *Y02A 50/411* (2018.01)

(58) Field of Classification Search
None
See application file for complete search history.

(56) References Cited

U.S. PATENT DOCUMENTS

| | | | | |
|---|---|---|---|---|
| 4,139,623 | A | 2/1979 | Jaeggi et al. | |
| 5,480,884 | A | 1/1996 | Thal et al. | |
| 5,756,524 | A | 5/1998 | Riordan et al. | |
| 6,022,884 | A * | 2/2000 | Mantlo et al. | 514/352 |
| 6,506,747 | B1 * | 1/2003 | Betageri | C07D 231/14 514/228.8 |
| 6,521,395 | B1 | 2/2003 | Begley et al. | |
| 6,777,432 | B1 | 8/2004 | Cutshall et al. | |
| 6,812,226 | B2 | 11/2004 | Baxter et al. | |
| 7,084,164 | B2 | 8/2006 | Tobe et al. | |
| 7,151,112 | B1 | 12/2006 | Cutshall et al. | |
| 7,176,310 | B1 | 2/2007 | Baughman et al. | |
| 7,482,355 | B2 | 1/2009 | Ebden et al. | |
| 7,759,373 | B2 | 7/2010 | Hongu et al. | |
| 8,748,623 | B2 | 6/2014 | Maeda et al. | |
| 2004/0110802 | A1 | 6/2004 | Thorarensen et al. | |
| 2004/0116479 | A1 | 6/2004 | Haviv et al. | |
| 2006/0063790 | A1 | 3/2006 | Gillman et al. | |
| 2006/0063930 | A1 * | 3/2006 | Agoston | C07D 205/04 544/162 |
| 2006/0276515 | A1 | 12/2006 | Cywin et al. | |
| 2007/0015734 | A1 | 1/2007 | McElroy et al. | |
| 2007/0078172 | A1 | 4/2007 | McElroy et al. | |
| 2009/0163463 | A1 | 6/2009 | Bruce et al. | |
| 2010/0210593 | A1 | 8/2010 | Maeda et al. | |

FOREIGN PATENT DOCUMENTS

| | | | |
|---|---|---|---|
| JP | H06-505027 | A | 6/1994 |
| JP | H09-510471 | A | 10/1997 |
| JP | 2007-119451 | A | 5/2007 |
| JP | 2008-510726 | A | 4/2008 |
| JP | 2008-511675 | A | 4/2008 |
| JP | 2008-540433 | A | 11/2008 |
| JP | 2010-508269 | A | 3/2010 |
| JP | 2010-510272 | A | 4/2010 |
| JP | 2010-525056 | A | 7/2010 |
| JP | 2013-536234 | A | 9/2013 |
| JP | 2016-164177 | A | 9/2016 |
| WO | WO 1993/010102 | A1 | 5/1993 |

(Continued)

OTHER PUBLICATIONS

Greco et al. "Combination therapy: Opportunities and challenges for polymer-drug conjugates as anticancer nanomedicines"Advanced Drug Delivery Reviews,2009, vol. 61, pp. 1203-1213.*

Ha et al. "Discovery of Novel CXCR2 Inhibitors Using Ligand-Based Pharmacophore Models" Journal of Chemical Information and Modeling, 2015, vol. 55, pp. 1720-1738.*

Silverman "The organic chemistry of drug design and drug action" Elsevier p. 29-32, 2004.

CAPLUS 1966:43814.

Patani et al.; "Bioisosterism; A Rational Approach in Drug Design"; Chem. Rev.; vol. 96; 1996; p. 3147-3176.

STN, RN# 1031968-79-2; Jul. 1, 2018; Aurora Fine Chemicals; 1 page.

STN, RN# 941285-77-4; Jul. 5, 2007; Stereosearch; 2 pages.

U.S. Appl. No. 15/469,395, filed Mar. 24, 2017, Maeda et al.

U.S. Appl. No. 15/177,218, filed Jun. 8, 2016, Maeda et al.

(Continued)

*Primary Examiner* — Alan D Diamond
(74) *Attorney, Agent, or Firm* — BakerHostetler

(57) ABSTRACT

There is disclosed [aminopyridine- and aminopyrimidinecarboxamide] *aminopyridinecarboxamide* compounds useful as pharmaceutical agents, synthesis processes, and pharmaceutical compositions which include [aminopyridine- and aminopyrimidinecarboxamides] *aminopyridinecarboxamide* compounds. More specifically, there is disclosed a genus of CXCR2 inhibitor compounds that are useful for treating a variety of inflammatory and neoplastic disorders.

24 Claims, No Drawings

(56) References Cited

FOREIGN PATENT DOCUMENTS

| | | | | |
|---|---|---|---|---|
| WO | WO 93/22312 | * | 11/1993 | ..... C07D 471/04 |
| WO | WO 1995/025723 | A1 | 9/1995 | |
| WO | WO 2001/021615 | A1 | 3/2001 | |
| WO | WO 2002/053544 | A1 | 7/2002 | |
| WO | WO 02053544 | A1 * | 7/2002 | |
| WO | 02053544 | | 11/2002 | |
| WO | 03024448 | | 3/2003 | |
| WO | WO 2003/024448 | A2 | 3/2003 | |
| WO | WO 0302448 | A2 * | 3/2003 | |
| WO | WO 2004/106296 | A2 | 12/2004 | |
| WO | WO 2006/023844 | A2 | 3/2006 | |
| WO | WO 2006/028958 | A2 | 3/2006 | |
| WO | WO 2006/121719 | A2 | 11/2006 | |
| WO | WO 2007/003962 | A2 | 1/2007 | |
| WO | WO 2007/026959 | A2 | 3/2007 | |
| WO | WO 2007/028082 | A1 | 3/2007 | |
| WO | WO 2007071358 | A1 * | 6/2007 | |
| WO | WO 2007/098352 | A2 | 8/2007 | |
| WO | WO 2008/057282 | A1 | 5/2008 | |
| WO | WO 2008/061795 | A2 | 5/2008 | |
| WO | WO 2008/073461 | A2 | 6/2008 | |
| WO | WO 2008073936 | A1 * | 6/2008 | |
| WO | 2008130320 | | 10/2008 | |
| WO | WO 2008/123469 | A1 | 10/2008 | |
| WO | WO 2008/130320 | A2 | 10/2008 | |
| WO | WO 2009/016088 | A1 | 2/2009 | |
| WO | 2009037503 | | 3/2009 | |
| WO | WO 2009/037503 | A2 | 3/2009 | |
| WO | WO 2009/071476 | A1 | 6/2009 | |
| WO | WO 2010/007382 | A1 | 1/2010 | |
| WO | WO 2010/032875 | A2 | 3/2010 | |
| WO | WO 2010/127978 | A1 | 11/2010 | |
| WO | WO 2011/025838 | A1 | 3/2011 | |
| WO | WO 2011/133888 | A1 | 10/2011 | |
| WO | WO 2012/027289 | A1 | 3/2012 | |

OTHER PUBLICATIONS

Brauch et al.; "Seven-component reactions by sequential chemoselective Ugi-Mumm/Ugi-Smiles reactions"; Chem. Commun.; vol. 46; 2010; p. 3387-3389.

Schuler et al.; Boronic Acid-Containing Aminopyridine- and Aminopyrimidinecarboxamide CXCR½ Antagonists: Optimization of Aqueous Solubility and Oral Bioavailability; Bioorganic & Medicinal Chemistry Letters; vol. 25(18); 2015; 16 pages.

Maeda et al.; "Boronic acid-containing CXCR½ antagonists; Optimization of metabolic stability, in vivo evaluation, and a proposed receptor binding model"; Bioorganic & Medicinal Chemistry Letters; vol. 25 No. 11; 2015; p. 2280-2284.

Chemical Abstracts; Registration No. 1203367-39-8; Jan. 4, 2010; Supplier: Ambinter.

Chemical Abstracts; Registration No. 1208091-29-5; Mar. 8, 2010; Supplier: AA ChemBio.

Chemical Abstracts; Registration No. 1208091-20-6; Mar. 8, 2010; Supplier: AA ChemBio.

Chemical Abstracts; Registration No. 1208090-09-8; Mar. 8, 2010; Supplier: AA ChemBio.

Chemical Abstracts; Registration No. 1208089-82-0; Mar. 8, 2010; Supplier: AA ChemBio.

Chemical Abstracts; Registration No. 1060540-20-6; Oct. 13, 2008; Supplier: ChemBridge Corporation.

CAPLUS 1967:443649.

CAPLUS 1978:443236.

CAPLUS 1986:148697.

CAPLUS 1988:454789.

CAPLUS 1988:528959.

Maeda et al. J. Pharm. Exp. Ther. 332:145-152, 2010.

Cowan et al.; "Metabolic N-Oxidation of 3-Substituted Pyridines: Identification of Products by Mass Spectrometry"; Biomedical Mass Spectrometry; vol. 5 No. 9; Sep. 1978; p. 551-556.

Khlebnikov et al.; "Quantitative structure-activity relationships for small non-peptide antagonists of CXCR2: Indirect 3D approach using the frontal polygon method"; Biorganic & Medicinal Chemistry; vol. 14 Issue 2; Jan. 2006; p. 352-365.

Kamath et al.; "Calculation of Relative Binding Free Energy Difference of DHFR Inhibitors by a Finite Difference Thermodynamic Integration (FDTI) Approach"; Journal of Biomolecular Structure & Dynamics; vol. 16 No. 6; 1991; p. 1239-1244.

Elworthy et al.; "N-Arylpiperazinyl-N'-propylamino Derivatives of Heteroaryl Amides as Functional Uroselective a1-Adrenoceptor Antagonists"; Journal of Medicinal Chemistry; vol. 40 No. 17; 1997; p. 2674-2687.

"3-Pyridinecarboxamide, N-methyl-N-(2-quinolinylmethyl)-6-[[(tetrahydro-2H-pyran-2-yl)methyl]amino]-"; Ambinter; RN 1203367-39-8; Jan. 24, 2010; 1 page.

Silverman, R. "The Organic Chemistry of Drug Design and Drug Action," 2004, Elsevier, pp. 29-32.*

CAPLUS 2002:521710.*

Cutshall et al. 1 "Nicotinanilides as inhibitors of neutraphil chemtaxis" Bioorg. Med. Chem. Lett. 12:1517-1520, 2002.

Cutshall et al. 2 "Nicotinamide N-oxides as CXCR2 antagonists" Bioorg. Med. Chem. Lett. 11:1951-1954, 2001.

de Kruijf et al. "Nonpeptidergic allosteric antagonists differentially bind to the CXCR2 chemokine receptor" J. Pharm. Exp. Ther. 329:783-790, 2009.

Nicholls et al. "Identification of a putative intracellular allosteric binding-site in the CXC chemokine receptors 1 and 2" Mol. Pharmacol. 74:1193-1202, 2008.

Busch-Petersen "Small molecule antagonists of the CXCR2 and CXCR1 chemokine receptors as therapeutic agents for the treatment of inflammatory diseases" Curr. Top. Med. Chem. 6:1345-1352, 2006.

* cited by examiner

AMINOPYRIDINECARBOXAMIDES AS CXCR2 MODULATORS

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

CROSS-REFERENCE TO RELATED PATENT APPLICATION

This [patent] *is a reissue* application [claims priority to U.S. Provisional Patent Application 61/376,224 filed on 23 Aug. 2010] *of U.S. Pat. No. 8,779,149, which issued Jul. 15, 2014, from U.S. patent application Ser. No. 13/215,014, filed Aug. 22, 2011, the disclosures of which are hereby incorporated by reference in their entirety.*

STATEMENT REGARDING FEDERALLY SPONSORED RESEARCH OR DEVELOPMENT

This invention was made with government support under grants 1R43HL072614, 5R44HL072614 awarded by the National Institutes of Health. The government has certain rights to this invention.

TECHNICAL FIELD

The present disclosure provides aminopyridine- and aminopyrimidinecarboxamides useful as pharmaceutical agents, synthesis processes, and pharmaceutical compositions which include aminopyridine- and aminopyrimidinecarboxamides compounds. More specifically, the present disclosure provides a genus of CXCR2 inhibitor compounds that are useful for treating a variety of inflammatory and neoplastic disorders.

BACKGROUND

Chemokines are chemotactic proteins that have the potential to attract macrophages, T-cells, eosinophils, basophils, neutrophils and endothelial cells to sites of inflammation and tumor growth. Chemokines are typically low molecular mass (7-9 kD) proteins that can be divided into four subfamilies: CC (or β-chemokines), CXC, C (or γ-chemokines) and CX3C (or δ-chemokines). The chemokines are categorized through their primary amino acid structure. The CXC subfamily is characterized by two conserved Cys residues (C) near the N-terminus and separated by an amino acid (X). The CXC-chemokines include, for example, interleukin-8 (IL-8), neutrophil-activating protein-1 (NAP-1), neutrophil-activating protein-2 (NAP-2), GROα, GROβ, GROγ, ENA-78, GCP-2, IP-10, MIG and PF4. The CXC subfamily of chemokines is further characterized by the presence or absence of a specific amino acid sequence, glutamic acid-leucine-arginine (or ELR for short) immediately before the first Cys residue of the CXC motif. Those chemokines with the ELR motif (ELRCXC) are important for the recruitment and activation of neutrophils to sites of inflammation. For example, GROα and IL-8 are ELRCXC chemokines.

The CXC-chemokines mediate their chemotactic activity through interaction with the chemokine receptors CXCR1 and CXCR2. CXCR1 binds IL-8 and GCP-2 with high affinity while CXCR2 binds all ELRCXC chemokines with high affinity.

Since CXC-chemokines promote the accumulation and activation of neutrophils, CXC-chemokines have been implicated in a wide range of acute and chronic inflammatory disorders including COPD, psoriasis and rheumatoid arthritis. (Baggiolini et al., FEBS Lett. 307:97,1992; Miller et al., Crit. Rev. Immunol. 12:17, 1992; Oppenheim et al., Annu. Rev. Immunol. 9:617, 1991; Seitz et al., J. Clin. Invest. 87:463, 1991; Miller et al., Am. Rev. Respir. Dis. 146:427, 1992; and Donnely et al., Lancet 341:643, 1998).

ELRCXC chemokines, including IL-8, GROα, GROβ, GROγ, NAP-2, and ENA-78 (Strieter et al. J. Biol. Chem. 270:27348-57, 1995), have also been implicated in the induction of tumor angiogenesis (new blood vessel growth). Angiogenic activity is due to ELRCXC-chemokine binding to, and activation of CXCR2, and possibly CXCR1 for IL-8, expressed on the surface of vascular endothelial cells (ECs) in surrounding vessels.

Many different types of tumors have been shown to produce ELRCXC chemokines. Chemokine production has been correlated with a more aggressive phenotype (Inoue et al. Clin. Cancer Res. 6:2104-2119, 2000) and poor prognosis (Yoneda et al. J. Nat. Cancer Inst. 90:447-454, 1998). Chemokines are potent chemotactic factors and the ELRCXC chemokines, in particular, have been shown to induce EC chemotaxis. Thus, these chemokines are thought to induce chemotaxis of endothelial cells toward their site of production in the tumor. This may be a critical step in the induction of angiogenesis by the tumor. Inhibitors of CXCR2 or dual inhibitors of CXCR2 and CXCR1 will inhibit the angiogenic activity of the ELRCXC chemokines and therefore block the growth of the tumor. This anti-tumor activity has been demonstrated for antibodies to IL-8 (Arenberg et al. J. Clin. Invest. 97:2792-2802, 1996), ENA-78 (Arenberg et al., J. Clin. Invest. 102:465-72, 1998), and GROα (Haghnegandar et al., J. Leukoc. Biology 67:53-62, 2000).

Therefore, there is a need in the art to find CXCR2 inhibitor compounds and modulator compounds that can be used as pharmaceutical compounds. There remains a need for compounds that are capable of modulating activity at CXC-chemokine receptors. For example, conditions associated with an increase in IL-8 production (which is responsible for chemotaxis of neutrophil and T-cell subsets into the inflammatory site and growth of tumors) would benefit by compounds that are inhibitors of IL-8 receptor binding. The present disclosure was made to satisfy this need.

SUMMARY

The disclosure provides a pharmaceutical composition comprising at least one compound of the formula (1) or a pharmaceutically acceptable salt, or solvate thereof and a pharmaceutically acceptable carrier. In certain embodiments, this disclosure provides a novel class of compounds that are CXC chemokine-modulators, pharmaceutical compositions comprising one or more of such compounds, and methods of treatment, prevention, inhibition, or amelioration of one or more diseases associated with CXC chemokine mediation using the compounds and compositions disclosed herein.

The present disclosure further provides a compound comprising formula (1) [or formula (2):]

(1)

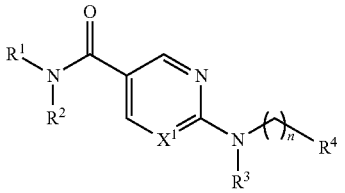

]

[(2)] (1)

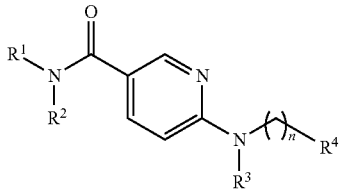

wherein $R^1$ [and] *is selected from the group consisting of hydrogen, 2-, 3-, or 4-halo-phenyl, heteroalkyl, n-propyl, isopropyl, n-butyl, t-butyl, n-pentyl, heptyl, nonyl, decyl, unsaturated alkyl, alkyl substituted with 1-4 substituents, aryl, arylalkyl, heteroaryl, heteroarylalkyl, cycloalkyl, cycloalkylalkyl, heterocyclyl, and heterocycloalkylalkyl;*

*wherein* $R^2$ [are independently] *is* selected from the group consisting of [hydrogen,] 2- or 3- or 4-halo-phenyl, [heteroalkyl, alkyl,] *ethyl, isopropyl, n-butyl, t-butyl, n-pentyl, heptyl, nonyl, decyl, unsaturated alkyl, alkyl substituted with 1-4 substituents selected from the group consisting of hydroxy, alkylamino, boronyl, carboxy, nitro, and cyano,* aryl, arylalkyl, heteroaryl, heteroarylalkyl, cycloalkyl, cycloalkylalkyl *comprising a monocyclic or multicyclic ring system comprising 3 to 5 or 7 to 10 carbon atoms*, heterocyclyl, and [heterocyclylalkyl] *heterocycloalkylalkyl, wherein aryl and heteroaryl are independently unsubstituted or substituted with one or more substituents selected from the group consisting of —C(O)R, —OR, aryl, —N(H)R, —N(R)R, —S—R, —B(R)R, —B(OH)$_2$, —B(OR)$_2$, —C(O)OH, —C(O)OR, —C(O)NH$_2$, —S(O)$_2$NH$_2$, —C(O)N(H)R, —C(O)N(R)R, —SH, —S—R, —NO$_2$, cyano, halo, haloalkyl, haloalkoxy, heterocyclyl, heteroalkyl, —OH, —OC(O)R, —C(O)R and —C(O)CH$_a$X$_b$, wherein a+b=3 and X is selected from the group consisting of F, Cl or Br, and wherein R is alkyl having less than twelve carbons*;

wherein $R^3$ [and] *is selected from the group consisting of hydrogen, heteroalkyl, methyl, n-propyl, isopropyl, n-butyl, t-butyl, n-pentyl, heptyl, nonyl, decyl, unsaturated alkyl, alkyl substituted with 1-4 substituents, aminoalkyl, aryl, arylalkyl, carboxyalkyl, heteroaryl, heteroarylalkyl, wherein the heteroaryl of the heteroarylalkyl is selected from pyridyl, pyrazinyl, furanyl, thienyl, pyrimidinyl, isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, and benzothiazolyl, cycloalkyl, cycloalkylalkyl, heterocyclyl, heterocycloalkylalkyl, —B($R^5R^6$), —BF$_3^-$M$^+$, —$R^7$—B($R^5R^6$), —$R^7$—BF$_3^-$M$^+$, —C(O)—$R^7$, —O—$R^7$, —S(O)$_y$—$R^7$ (wherein y=0, 1, or 2), —P(O)—($R^5R^6$), —N($R^8R^9$), carboxylates, amines, phosphonates, and phosphates;*

*wherein* $R^4$ [are independently] *is* selected from the group consisting of [hydrogen, heteroalkyl, alkyl,] *isopropyl, n-butyl, n-pentyl, heptyl, nonyl, decyl, unsaturated alkyl,* aminoalkyl, [aryl, arylalkyl,] carboxyalkyl, [heteroaryl,] heteroarylalkyl, *substituted* cycloalkyl, *unsubstituted cycloalkyl of 5 to 7 ring carbons,* cycloalkylalkyl, heterocyclyl, and [heterocyclylalkyl, or $R^3$ and $R^4$ are independently an ionizing group selected from the group consisting of carboxylates, amines,] *heterocycloalkylalkyl, wherein the heterocyclic ring of the heterocycloalkylalkyl is selected from piperidyl, morpholinyl, thiomorpholinyl, thiazolidinyl, 1,3-dioxolanyl, 1,4-dioxolanyl, tetrahydrofuranyl, tetrahydrothiophenyl, and tetrahydrothiopyranyl* phosphonates, [and] phosphates, *B($R^5R^6$), —BF$_3^-$M$^+$, —$R^7$—B($R^5R^6$), —$R^7$—BF$_3^-$M$^+$, —C(O)—$R^{10}$, —O—$R^7$, —S(O)$_y$—$R^7$ (wherein y=0, 1, or 2), —P(O)—($R^5R^6$), —N($R^8R^9$), aryl substituted with one or more substituents selected from the group consisting of —C(O)R, —OCF$_3$, —O-ethyl, —O-propyl, —O-butyl, —O-pentyl, —O-hexyl, —O-heptyl, —O-octyl, —O-nonyl, —O-decyl, —O-undecyl, —O-dodecyl, —CF$_3$, ethyl, propyl, butyl, pentyl, hexyl, heptyl, octyl, nonyl, decyl, undecyl, dodecyl, aryl, —N(H)R, —N(R)R, —S—R, —NH$_2$, —N$_3$, —B(R)R, —B(OH)$_2$, —B(OR)$_2$, —C(O)OH, —C(O)OR, —C(O)NH$_2$, —S(O)$_2$NH$_2$, —C(O)N(H)R, —C(O)N(R)R, —SH, —S—R, —NO$_2$, cyano, halo, haloalkyl, haloalkoxy, heterocyclyl, heteroalkyl, —OH, —OC(O)R, —C(O)R and —C(O)CH$_a$X$_b$, wherein a+b=3 and X is selected from the group consisting of F, Cl or Br, and wherein R is alkyl having less than twelve carbons, and heteroaryl, wherein the heteroaryl is selected from the group consisting of pyridyl, pyrazinyl, furanyl, thienyl, pyrimidinyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, imidazo(1,2-a)pyridinyl, imidazo(2,1-b)thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, and benzothiazolyl, and wherein the heteroaryl is unsubstituted or substituted by one or more substituents selected from acyl, alkoxy, aryl, aminoalkyl, alkylthio, amino, azido, boronyl, carboxy, alkoxycarbonyl, aminocarbonyl, aminosulfonyl, alkylaminocarbonyl, cyano, halo, haloalkyl, haloalkoxy, heterocyclyl, heteroalkyl, hydroxyl, acyloxy, ketone, substituted halomethylketone, mercapto, and nitro*;

[wherein $R^3$ and $R^4$ are also selected from the group consisting of —B($R^5R^6$), —BF$_3^-$M$^+$, —$R^7$—B($R^5R^6$), —$R^7$—BF$_3^-$M$^+$, $R^7$,—C(O)—$R^7$, —O—$R^7$, —S(O)$_y$—$R^7$ (wherein y=0, 1, or 2), —P(O)—($R^5R^6$) and —N($R^8R^9$);]

wherein $R^7$ is selected from the group consisting of alkyl, aryl, arylalkyl, cycloalkyl, heteroaryl, heteroarylalkyl, heterocyclyl and [heterocyclylalkyl] *heterocycloalkylalkyl*;

wherein $M^+$ is a Group I or a Group II metal;

wherein $R^5$ and $R^6$ are independently selected from the group consisting of hydrogen, hydroxyl, aryloxy, or alkoxy, or wherein $R^5$ and $R^6$ together form a cyclic ester, or an acid anhydride (either mixed or symmetrical);

wherein $R^8$ [and $R^9$ are independently] *is* selected from the group consisting of hydrogen, alkyl, haloalkyl, aryl, cycloalkyl, arylalkyl, heteroalkyl, [hetercyclyl] *heterocyclyl* and [heterocyclylalkyl] *heterocycloalkylalkyl*; *and wherein $R^9$ is selected from haloalkyl, aryl, cycloalkyl, arylalkyl, heteroalkyl, heterocyclyl and heterocycloalkylalkyl;* $R^8$ and $R^9$ are both oxygen to form a nitro group; or $R^8$ and $R^9$ together with the nitrogen to which they are attached, form a heterocyclyl; and

[wherein $X^1$ is carbon or nitrogen; and] pharmaceutical compositions thereof.

*The present disclosure further provides a compound comprising a compound from formula (1):*

(1)

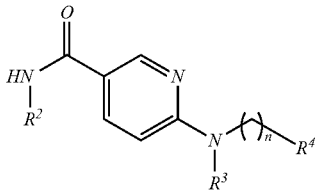

*wherein $R^2$ is 2-, 3-, or 4-halophenyl;*

*wherein $R^3$ is hydrogen, heteroalkyl, alkyl, aminoalkyl, aryl, arylalkyl, carboxyalkyl, heteroaryl, heteroarylalkyl, cycloalkyl, cycloalkylalkyl, heterocyclyl, heterocycloalkylalkyl, carboxylate, amine, phosphonate, phosphate, —$B(R^5R^6)$, —$BF_3^-M^+$, —$R^7$—$B(R^5R^6)$, —$R^7$—$BF_3^-M^+$, —$C(O)$—$R^7$, —$O$—$R^7$, —$S(O)_y$—$R^7$ (wherein y=0, 1, or 2), —$P(O)$—$(R^5R^6)$, —$N(R^8R^9)$,*

*wherein $R^4$ is heteroalkyl, n-propyl, isopropyl, n-butyl, t-butyl, n-pentyl, heptyl, nonyl, decyl, unsaturated alkyl, alkyl substituted with 1-4 substituents, aminoalkyl, naphthyl, indenyl, tetrahydronaphthyl, indanyl, anthracenyl, fluorenyl, substituted aryl, arylalkyl, carboxyalkyl, heteroaryl, heteroarylalkyl, substituted cycloalkyl, unsubstituted cycloalkyl of 5 to 7 ring carbons, cycloalkylalkyl, heterocyclyl, heterocycloalkylalkyl, carboxylate, amine, phosphonate, phosphate, —$B(R^5R^6)$, —$BF_3^-M^+$, —$R^7$—$B(R^5R^6)$, —$R^7BF_3^-M^+$, —$C(O)$—$R^7$, —$O$—$R^7$, —$S(O)_y$—$R^7$ (wherein y=0, 1, or 2), —$P(O)$—$(R^5R^6)$, or —$N(R^8R^9)$; wherein $M^+$ is a Group I or a Group II metal;*

*wherein $R^5$ and $R^6$ are independently hydrogen, hydroxyl, aryloxy, or alkoxy, or wherein $R^5$ and $R^6$ together form a cyclic ester, or an acid anhydride (either mixed or symmetrical);*

*wherein $R^7$ is alkyl, aryl, arylalkyl, cycloalkyl, heteroaryl, heteroarylalkyl, heterocyclyl or heterocycloalkylalkyl;*

*wherein $R^8$ and $R^9$ are independently hydrogen, alkyl, haloalkyl, aryl, cycloalkyl, arylalkyl, heteroalkyl, heterocyclyl or heterocycloalkylalkyl; $R^8$ and $R^9$ are both oxygen to form a nitro group; or $R^8$ and $R^9$ together with the nitrogen to which they are attached form a heterocyclyl; and*

*wherein n is 1;*

*a pharmaceutically acceptable solvated or unsolvated form thereof; a pharmaceutically acceptable salt thereof; or a pharmaceutical composition thereof.*

*The present disclosure further provides a compound comprising a compound from formula (1):*

(1)

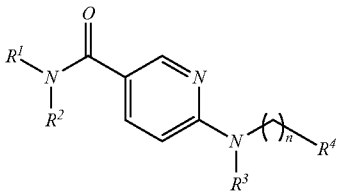

*wherein $R^1$ is hydrogen, 2- or 3- or 4-halo-phenyl, heteroalkyl, methyl, ethyl, isopropyl, butyl, pentyl, hexyl, heptyl, octyl, nonyl, decyl, undecyl, dodecyl, aryl, arylalkyl, heteroaryl, heteroarylalkyl, cycloalkyl, cycloalkylalkyl, heterocyclyl, or heterocycloalkylalkyl;*

*wherein $R^2$ is 2- or 3- or 4-halo-phenyl, methyl, ethyl, isopropyl, butyl, pentyl, hexyl, heptyl, octyl, nonyl, decyl, undecyl, dodecyl, aryl, arylalkyl, heteroaryl, heteroarylalkyl, cycloalkyl, cycloalkylalkyl, heterocyclyl, or heterocycloalkylalkyl;*

*wherein $R^3$ is hydrogen, heteroalkyl, alkyl, aminoalkyl, aryl, arylalkyl, carboxyalkyl, heteroaryl, heteroarylalkyl, wherein the heteroaryl of the heteroarylalkyl is selected from pyridyl, pyrazinyl, furanyl, thienyl, pyrimidinyl, isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, and benzothiazolyl, cycloalkyl, cycloalkylalkyl, heterocyclyl, heterocycloalkylalkyl, carboxylate, amine, phosphonate, or phosphate;*

*wherein $R^4$ is —$B(R^5R^6)$, —$BF_3^-M^+$, —$R^7$—$B(R^5R^6)$, —$R^7$—$BF_3^-M^+$, —$C(O)$—$R^7$, —$O$—$R^7$, —$S(O)_y$—$R^7$ (wherein y=0, 1, or 2), —$P(O)$—$(R^5R^6)$, —$N(R^8R^9)$, cycloalkyl, piperidyl, pyrrolidinyl, piperazinyl, morpholinyl, thiomorpholinyl, thiazolidinyl, 1,3-dioxolanyl, 1,4-dioxanyl, tetrahydrofuranyl, tetrahydrothiophenyl, tetrahydrothiopyranyl, heterocycloalkylalkyl, wherein the heterocyclic ring of the heterocycloalkylalkyl is selected from piperidyl, pyrrolidinyl, morpholinyl, thiomorpholinyl, thiazolidinyl, 1,3-dioxolanyl, 1,4-dioxanyl, tetrahydrofuranyl, tetrahydropyranyl, tetrahydrothiophenyl, tetrahydrothiopyranyl, or an aryl substituted with a chloride, bromide, iodide, —OH, —$OC(O)R$, —$OCF_3$, —$C(O)R$, —$CF_3$, ethyl, propyl, butyl, pentyl, hexyl, heptyl, octyl, nonyl, decyl, undecyl, dodecyl, —$NO_2$, or —$B(R^5R^6)$, wherein R is methyl, ethyl, n-propyl, butyl, pentyl, hexyl, heptyl, octyl, nonyl, decyl, undecyl, or dodecyl, and $M^+$ is a Group I or a Group II metal;*

*wherein $R^5$ and $R^6$ are independently hydrogen, hydroxyl, aryloxy, or alkoxy, or wherein $R^5$ and $R^6$ together form a cyclic ester, or an acid anhydride (either mixed or symmetrical);*

*wherein $R^7$ is alkyl, aryl, arylalkyl, cycloalkyl, heteroaryl, heteroarylalkyl, heterocyclyl or heterocycloalkylalkyl;*

*wherein $R^8$ and $R^9$ are independently hydrogen, alkyl, haloalkyl, aryl, cycloalkyl, arylalkyl, heteroalkyl, heterocyclyl or heterocycloalkylalkyl; $R^8$ and $R^9$ are both oxygen to form a nitro group; or $R^8$ and $R^9$ together with the nitrogen to which they are attached form a heterocyclyl; and*

*wherein n is 1; or*

*a pharmaceutically acceptable solvated or unsolvated form thereof; a pharmaceutically acceptable salt thereof; or a pharmaceutical composition thereof.*

Preferably, $X^1$ is carbon. Preferably, $R^1$ is hydrogen and $R^2$ is 4-fluoro-phenyl. Preferably, $R^3$ is either hydrogen or methyl. Preferably, $R^4$ is 4-phenylboronic acid.

[The present disclosure further provides a pharmaceutical composition comprising a compound of formula (1) or formula (2):]

[The present disclosure further provides a compound comprising formula (1) or formula (2):

(1)

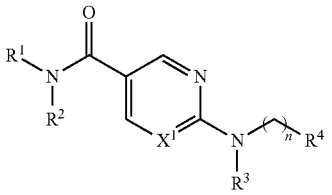

(2)

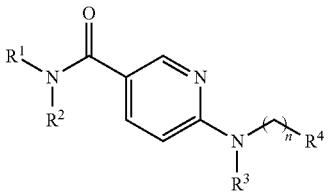

]

[wherein $R^1$ and $R^2$ are independently selected from the group consisting of hydrogen, 2- or 3- or 4-halo-phenyl, heteroalkyl, alkyl, aryl, arylalkyl, heteroaryl, heteroarylalkyl, cycloalkyl, cycloalkylalkyl, heterocyclyl, and heterocyclylalkyl;]

[wherein $R^3$ and $R^4$ are independently selected from the group consisting of hydrogen, heteroalkyl, alkyl, aminoalkyl, aryl, arylalkyl, carboxyalkyl, heteroaryl, heteroarylalkyl, cycloalkyl, cycloalkylalkyl, heterocyclyl, and heterocyclylalkyl, or $R^3$ and R4 are independently an ionizing group selected from the group consisting of carboxylates, amines, phosphonates, and phosphates; $R^3$ may be also equivalent to $R^4$;]

[wherein $R^3$ and $R^4$ are also selected from the group consisting of —$B(R^5R^6)$, —$BF_3^-M^+$, $R^7$—$B(R^5R^6)$, —$R^7$—$BF_3^-M^+$, $R^7$,—C(O)—$R^7$, —O—$R^7$, —$S(O)_y$—$R^7$ (wherein y=0, 1, or 2), —P(O)—$(R^5R^6)$ and —$N(R^8R^9)$;]

[wherein $R^7$ is selected from the group consisting of alkyl, aryl, arylalkyl, cycloalkyl, heteroaryl, heteroarylalkyl, heterocyclyl and heterocyclylalkyl;]

[wherein $M^+$ is a Group I or a Group II metal;]

[wherein $R^5$ and $R^6$ are independently selected from the group consisting of hydrogen, hydroxyl, aryloxy, or alkoxy, or wherein $R^5$ and $R^6$ together form a cyclic ester, or an acid anhydride (either mixed or symmetrical);]

[wherein $R^8$ and $R^9$ are independently selected from the group consisting of hydrogen, alkyl, haloalkyl, aryl, cycloalkyl, arylalkyl, heteroalkyl, hetercyclyl and heterocyclylalkyl; $R^8$ and $R^9$ are both oxygen to form a nitro group; or $R^8$ and $R^9$ together with the nitrogen to which they are attached, form a heterocyclyl; and]

[wherein $X^1$ is carbon or nitrogen; and pharmaceutical compositions thereof.]

[Preferably, $X^1$ is carbon. Preferably, $R^1$ is hydrogen and $R^2$ is 4-fluoro-phenyl. Preferably, $R^3$ is either hydrogen or methyl. Preferably, $R^4$ is 4-phenylboronic acid.]

The present disclosure provides a method for treating a disease or disorder selected from the group consisting of pain (e.g., acute pain, acute inflammatory pain, chronic inflammatory pain, and neuropathic pain), acute inflammation, chronic inflammation, rheumatoid arthritis, psoriasis, atopic dermatitis, asthma, bronchopulmonary dysplasia, COPD, adult respiratory disease, arthritis, inflammatory bowel disease, Crohn's disease, ulcerative colitis, septic shock, endotoxic shock, gram negative sepsis, toxic shock syndrome, stroke, ischemia reperfusion injury, renal reperfusion injury, glomerulonephritis, thrombosis, Alzheimer's disease, graft vs. host reaction (i.e., graft-versus-host disease), allograft rejections (e.g., acute allograft rejection, and chronic allograft rejection), malaria, acute respiratory distress syndrome, delayed type hypersensitivity reaction, atherosclerosis, cerebral ischemia, cardiac ischemia, osteoarthritis, multiple sclerosis, restinosis, angiogenesis, angiogenesis associated with tumor growth, osteoporosis, gingivitis, respiratory viruses, herpes viruses, hepatitis viruses, HIV, Kaposi's sarcoma associated virus (i.e., Kaposi's sarcoma), meningitis, cystic fibrosis, pre-term labor, cough, pruritis, multi-organ dysfunction, trauma, strains, sprains, contusions, psoriatic arthritis, herpes, encephalitis, CNS vasculitis, traumatic brain injury, systemic tumors, CNS tumors, tumors dependent on angiogenesis for growth, leukopenia and neutropenia, chemotherapy-induced leukopenia and neutropenia, opportunistic infections associated with neutropenia or leukopenia, subarachnoid hemorrhage, post surgical trauma, interstitial pneumonitis, hypersensitivity, crystal induced arthritis, acute pancreatitis, chronic pancreatitis, acute alcoholic hepatitis, necrotizing enterocolitis, chronic sinusitis, angiogenic ocular disease, ocular inflammation, retinopathy of prematurity, diabetic retinopathy, macular degeneration with the wet type preferred, corneal neovascularization, polymyositis, vasculitis, acne, gastric ulcers, duodenal ulcers, celiac disease, esophagitis, glossitis, airflow obstruction, airway hyperresponsiveness (i.e., airway hyperreactivity), bronchiectasis, bronchiolitis, bronchiolitis obliterans, chronic bronchitis, cor pulmonae, dyspnea, emphysema, hypercapnea, hyperinflation, hypoxemia, hyperoxia-induced inflammations, hypoxia, surgical lung volume reduction, pulmonary fibrosis, pulmonary hypertension, right ventricular hypertrophy, peritonitis associated with continuous ambulatory peritoneal dialysis (CAPD), granulocytic ehrlichiosis, sarcoidosis, small airway disease, ventilation-perfusion mismatching, wheeze, colds, gout, alcoholic liver disease, lupus, burn therapy (i.e., the treatment of burns), periodontitis, cancer, transplant reperfusion injury, and early transplantation rejection (e.g., acute allograft rejection) in a patient in need of such treatment, comprising administering an effective amount of a compound of formula (1) [or formula (2):]

(1)

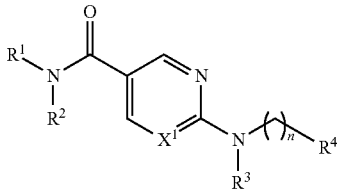

]

[(2)] *(1)*

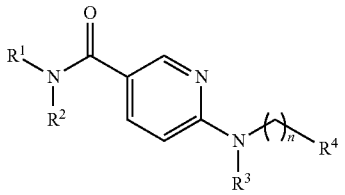

wherein $R^1$ and $R^2$ are independently selected from the group consisting of hydrogen, 2- or 3- or 4-halo-phenyl, heteroalkyl, alkyl, aryl, arylalkyl, heteroaryl, heteroarylalkyl, cycloalkyl, cycloalkylalkyl, heterocyclyl, and heterocyclylalkyl;

wherein $R^3$ and $R^4$ are independently selected from the group consisting of hydrogen, heteroalkyl, alkyl, aminoalkyl, aryl, arylalkyl, carboxyalkyl, heteroaryl, heteroarylalkyl, cycloalkyl, cycloalkylalkyl, heterocyclyl, and heterocyclylalkyl, or $R^3$ is an ionizing group selected from the group consisting of carboxylates, amines, phosphonates, and phosphates;

wherein $R^3$ and $R^4$ are also independently selected from —$B(R^5R^6)$, —$BF_3^-M^+$, —$R^7$—$B(R^5R^6)$, —$R^7$—$BF_3^-M^+$, $R^7$,—C(O)—$R^7$, —O—$R^7$, —$S(O)_y$—$R^7$ (wherein y=0, 1, or 2), —P(O)—$(R^5R^6)$ and —$N(R^8R^9)$;

wherein $R^7$ is selected from the group consisting of alkyl, aryl, arylalkyl, cycloalkyl, heteroaryl, heteroarylalkyl, heterocyclyl and heterocyclylalkyl;

wherein $M^+$ is a Group I or a Group II metal;

wherein $R^5$ and $R^6$ are independently selected from the group consisting of hydrogen, hydroxyl, aryloxy, or alkoxy, or wherein $R^5$ and $R^6$ together form a cyclic ester, or an acid anhydride (either mixed or symmetrical);

wherein $R^8$ and $R^9$ are independently selected from the group consisting of hydrogen, alkyl, haloalkyl, aryl, cycloalkyl, arylalkyl, heteroalkyl, hetercyclyl and heterocyclylalkyl; $R^8$ and $R^9$ are both oxygen to form a nitro group; or $R^8$ and $R^9$ together with the nitrogen to which they are attached, form a heterocyclyl; and

[wherein $X^1$ is carbon or nitrogen; and] pharmaceutical compositions thereof.

[Preferably, $X^1$ is carbon.] Preferably, $R^1$ is hydrogen and $R^2$ is 4-fluoro-phenyl. Preferably, $R^3$ is either hydrogen or methyl. Preferably, $R^4$ is 4-phenylboronic acid.

DETAILED DESCRIPTION

Definitions

When any substituent or variable occurs more than one time in any moiety, its definition on each occurrence is independent of its definition at every other occurrence. Also, combinations of substituents and/or variables are permissible only if such combinations result in stable compounds.

Unless indicated otherwise, the following definitions apply throughout the present specification and claims. These definitions apply regardless of whether a term is used by itself or in combination with other terms. For example, the definition of "alkyl" also applies to the "alkyl" portion of the defined term "alkoxy."

"An effective amount" or a "therapeutically effective amount" means to describe an amount of compound of the present disclosure or another agent effective to treat a mammal (e.g., a human) having a disease or CXC chemokine-mediated condition, and thus producing the desired therapeutic effect.

"At least one" means one or more (e.g., 1-3, 1-2, or 1).

"Composition" includes a product comprising the specified ingredients in the specified amounts, as well as any product that results, directly or indirectly, from combination of the specified ingredients in the specified amounts.

"In combination with" as used to describe the administration of a compound of formula (1) with other medicaments in the methods of treatment of this invention, means that the compounds of formula (1) and formula (2) and the other medicaments are administered sequentially or concurrently in separate dosage forms, or are administered concurrently in the same dosage form.

"Mammal" means a human or other mammal, or means a human being.

"Patient" includes both human and other mammals, preferably human.

"Prodrug" denotes a compound that is a drug precursor which, upon administration to a subject, undergoes chemical conversion by metabolic or chemical processes to yield a compound of either formula (1) or formula (2) or a salt and/or solvate thereof. A discussion of pro-drugs is provided in T. Higuchi and V. Stella, Pro-drugs as Novel Delivery Systems, Volume 14 of the A.C.S. Symposium Series, and in Bioreversible Carriers in Drug Design, Edward B. Roche, ed., American Pharmaceutical Association and Pergamon Press, 1987, both of which are incorporated herein by reference.

"Alkyl" is a saturated or unsaturated, straight or branched, hydrocarbon chain. In various embodiments, the alkyl group has 1-18 carbon atoms, i.e. is a $C_1$-$C_{18}$ group, or is a $C_1$-$C_{12}$ group, a $C_1$-$C_6$ group, or a $C_1$-$C_4$ group. A lower alkyl group has 1-6 carbons. Independently, in various embodiments, the alkyl group has zero branches (i.e., is a straight chain), one branch, two branches, or more than two branches. Independently, in one embodiment, the alkyl group is saturated. In another embodiment, the alkyl group is unsaturated. In various embodiments, the unsaturated alkyl may have one double bond, two double bonds, more than two double bonds, and/or one triple bond, two triple bonds, or more than two triple bonds. Alkyl chains may be optionally substituted with 1 substituent (i.e., the alkyl group is mono-substituted), or 1-2 substituents, or 1-3 substituents, or 1-4 substituents, etc. The substituents may be selected from the group consisting of hydroxy, amino, alkylamino, boronyl, carboxy, nitro, cyano, and the like. When the alkyl group incorporates one or more heteroatoms, the alkyl group is referred to herein as a heteroalkyl group. When the substituents on an alkyl group are hydrocarbons, then the resulting group is simply referred to as a substituted alkyl. In various aspects, the alkyl group including substituents has less then 25, 24, 23, 22, 21, 20, 19, 18, 17, 16, 15, 14, 13, 12, 11, 10, 9, 8, or 7 carbons.

"Lower alkyl" means a group having about 1 to about 6 carbon atoms in the chain which chain may be straight or branched. Non-limiting examples of suitable alkyl groups include methyl, ethyl, n-propyl, isopropyl, n-butyl, t-butyl, n-pentyl, heptyl, nonyl, and decyl.

"Alkoxy" means an alkyl-O-group wherein alkyl is as defined above. Non-limiting examples of alkoxy groups include: methoxy, ethoxy, n-propoxy, isopropoxy, n-butoxy and heptoxy. The bond to the parent moiety is through the ether oxygen.

"Alkoxyalkyl" means an alkoxy-alkyl-group in which the alkoxy and alkyl are as previously described. Preferred alkoxyalkyl comprise a lower alkyl group. The bond to the parent moiety is through the alkyl.

"Alkylaryl" means an alkyl-aryl-group in which the alkyl and aryl are as previously described. Preferred alkylaryls comprise a lower alkyl group. The bond to the parent moiety is through the aryl.

"Aminoalkyl" means an $NH_2$-alkyl-group, wherein alkyl is as defined above, bound to the parent moiety through the alkyl group.

"Aryl" (sometimes abbreviated "Ar") is an aromatic carbocyclic hydrocarbon ring system. The ring system may be monocyclic or fused polycyclic (e.g., bicyclic, tricyclic, etc.). In one embodiment, the aryl group is monocyclic, and is preferably a $C_6$ ring system, i.e. a phenyl ring is a preferred aryl ring, where preferred bicyclic aryl rings are $C_8$-$C_{12}$, or $C_9$-$C_{10}$. A naphthyl ring, which has 10 carbon atoms, is a preferred polycyclic aryl ring. Unless otherwise indicated herein, the term "aryl" as used herein is meant to include aryl rings optionally substituted by one or more substituents selected from acyl (—C(O)—R), alkoxy (—O—R), alkyl, aryl, alkylamino (—N(H)—R and —N(R)R), alkylthio (—S—R), amino (—$NH_2$), azido (—$N_3$), boronyl (—B(R)R or —$B(OH)_2$ or —$B(OR)_2$), carboxy (—C(O)—OH), alkoxycarbonyl (—C(O)—OR), aminocarbonyl (—C(O)—$NH_2$), aminosulfonyl (—$S(O)_2$—$NH_2$), alkylaminocarbonyl (—C(O)—N(H)R and —C(O)—N(R)R), cyano, halo (fluoro, bromo, chloro, iodo), haloalkyl, haloalkoxy, heterocyclyl, heteroalkyl, hydroxyl (—OH), acyloxy (—O—C(O)—R), ketone (—C(O)—R), substituted halomethylketone (—C(O)—$CH_mX_n$, where m+n=3, X=F, Cl, Br), mercapto (—SH and —S—R) and nitro (—$NO_2$) where each R group is an alkyl group having less than about 12 carbons, preferably where the R group is a lower alkyl group. Non-limiting examples of suitable aryl groups include: phenyl, naphthyl, indenyl, tetrahydronaphthyl, indanyl, anthracenyl, and fluorenyl.

"Arylalkyl" refers to an alkyl group as defined substituted by one or more aryl groups as defined below. Phenyl and naphthyl are preferred aryl groups in an arylalkyl group. A preferred alkyl group is methyl, so that a preferred arylalkyl group is benzyl or benzyl having one or more substituents on the phenyl ring. Unless otherwise indicated, the term "arylalkyl" as used herein is meant to include arylalkyl groups wherein the aryl ring therein is optionally substituted by one or more substituents selected from acyl (—C(O)—R), alkoxy (—O—R), alkyl, aryl, alkylamino (—N(H)—R and —N(R)R), alkylthio (—S—R), amino (—$NH_2$), azido (—$N_3$), boronyl (—B(R)R or —$B(OH)_2$ or —$B(OR)_2$), carboxy (—C(O)—OH), alkoxycarbonyl (—C(O)—OR), aminocarbonyl (—C(O)—$NH_2$), aminosulfonyl (—$S(O)_2$—$NH_2$), alkylaminocarbonyl (—C(O)—N(H)R and —C(O)—N(R)R), cyano, halo (fluoro, bromo, chloro, iodo), haloalkyl, haloalkoxy, heterocyclyl, heteroalkyl, hydroxyl (—OH), acyloxy (—O—C(O)—R), ketone (—C(O)—R), substituted halomethylketone (—C(O)—$CH_mX_n$, where m+n=3, X=F, Cl, Br), mercapto (—SH and —S—R) and nitro (—$NO_2$) where each R is an alkyl group having less than about 12 carbons, preferably where the R group is a lower alkyl group.

"Arylalkyl" means an aryl-alkyl-group in which the aryl and alkyl are as previously described. Preferred arylalkyls comprise a lower alkyl group. Non-limiting examples of suitable aralkyl groups include benzyl, 2-phenethyl and napthalenylmethyl. The bond to the parent moiety is through the alkyl.

"Aryloxy" means an aryl-O-group in which the aryl group is as previously described. Non-limiting examples of suitable aryloxy groups include phenoxy and naphthoxy. The bond to the parent moiety is through the ether oxygen.

"Carboxyalkyl" means an HOOC-alkyl-group, wherein alkyl is as defined above, bound to the parent moiety through the alkyl group.

"Chemokine" means a protein molecule involved in chemotaxis.

A "chemokine-mediated disease" means a disease in which at least one element or cause is related to regulation of a CXC chemokine.

"Commercially available chemicals" and the chemicals used in the Examples set forth herein may be obtained from standard commercial sources, where such sources include, for example, Acros Organics (Pittsburgh, Pa.), Sigma-Adrich Chemical (Milwaukee, Wis.), Avocado Research (Lancashire, U.K.), Bionet (Cornwall, U.K.), Boron Molecular (Research Triangle Park, N.C.), Combi-Blocks (San Diego, Calif.), Eastman Organic Chemicals, Eastman Kodak Company (Rochester, N.Y.), Fisher Scientific Co. (Pittsburgh, Pa.), Frontier Scientific (Logan, Utah), ICN Biomedicals, Inc. (Costa Mesa, Calif.), Lancaster Synthesis (Windham, N.H.), Maybridge Chemical Co. (Cornwall, U.K.), Pierce Chemical Co. (Rockford, Ill.), Riedel de Haen (Hannover, Germany), Spectrum Quality Product, Inc. (New Brunswick, N.J.), TCI America (Portland, Oreg.), and Wako Chemicals USA, Inc. (Richmond, Va.).

"Compounds described in the chemical literature" may be identified through reference books and databases directed to chemical compounds and chemical reactions, as known to one of ordinary skill in the art. Suitable reference books and treatise that detail the synthesis of reactants useful in the preparation of compounds disclosed herein, or provide references to articles that describe the preparation of compounds disclosed herein, include for example, "Synthetic Organic Chemistry", John Wiley and Sons, Inc. New York; S. R. Sandler et al, "Organic Functional Group Preparations," $2^{nd}$ Ed., Academic Press, New York, 1983; H. O. House, "Modern Synthetic Reactions," $2^{nd}$ Ed., W. A. Benjamin, Inc. Menlo Park, Calif., 1972; T. L. Glichrist, "Heterocyclic Chemistry," $2^{nd}$ Ed. John Wiley and Sons, New York, 1992; J. March, "Advanced Organic Chemistry: reactions, Mechanisms and Structure," $5^{th}$ Ed., Wiley Interscience, New York, 2001; Specific and analogous reactants may also be identified through the indices of known chemicals prepared by the Chemical Abstract Service of the American Chemical Society, which are available in most public and university libraries, as well as through online databases (the American Chemical Society, Washington, D.C. www.acs.org may be contacted for more details). Chemicals that are known but not commercially available in catalogs may be prepared by custom chemical synthesis houses, where many of the standard chemical supply houses (such as, those listed above) provide custom synthesis services.

"Cycloalkyl" means a non-aromatic mono-or multicyclic ring system comprising about 3 to about 10 carbon atoms, preferably about 5 to about 10 carbon atoms. Preferred cycloalkyl rings contain about 5 to about 7 ring atoms. A multicyclic cycloalkyl substituent may include fused, spiro, or bridged ring structures. Non-limiting examples of suitable monocyclic cycloalkyls include cyclopropyl, cyclobutyl, cyclopentyl, cyclohexyl, cycloheptyl and the like. Non-limiting examples of suitable multicyclic cycloalkyls include 1-decalin, norbornyl, adamantly and the like. Cycloalkyl substituents may be substituted or unsubstituted. In one embodiment, the cycloalkyl is unsubstituted. In another embodiment, the cycloalkyl is substituted with, e.g., 1 substituent (i.e., the cycloalkyl group is mono-substituted), or 1-2 substituents, or 1-3 substituents, or 1-4 substituents, etc. In one embodiment, the substituents that may be present on the cycloalkyl aliphatic ring are selected from acyl (—C(O)—R), alkoxy (—O—R), alkyl, aryl, alkylamino (—N(H)—R and —N(R)R), alkylthio (—S—R), amino (—$NH_2$), azido (—$N_3$), boronyl (—B(R)R or —$B(OH)_2$ or —$B(OR)_2$), carboxy (—C(O)—OH), alkoxycarbonyl (—C(O)—OR), aminocarbonyl (—C(O)—$NH_2$), aminosulfonyl (—$S(O)_2$—$NH_2$), alkylaminocarbonyl (—C(O)—N(H)R and —C(O)—N(R)R), cyano, halo (fluoro, bromo, chloro, iodo), haloalkyl, haloalkoxy, heterocyclyl, heteroalkyl, hydroxyl (—OH), acyloxy (—O—C(O)—R), ketone (—C(O)—R), substituted halomethylketone (—C(O)—$CH_mX_n$, where m+n=3, X=F, Cl, Br), mercapto (—SH and —S—R) and nitro (—$NO_2$) In one aspect the R group in the above substituents is an alkyl group having less than about 12 carbons, while in another aspect the R group is a lower alkyl group.

"Cycloalkylalkyl" means a cycloalkyl group bound to the parent moiety through an alkyl group. Non-limiting examples include: cyclopropylmethyl and cyclohexylmethyl.

"Cycloalkylaryl" means a cycloalkyl group bound to the parent moiety through an aryl group. Non-limiting examples include: cyclopropylphenyl and cyclohexylphenyl.

"Effective amount" or "therapeutically effective amount" is meant to describe an amount of compound or a composition of the present disclosure effective in decreasing or increasing (i.e., modulating) the action of a CXC chemokine at a CXC chemokine receptor and thus producing the desired therapeutic effect in a suitable patient.

"Fluoroalkoxy" means an alkoxy group as defined above wherein one or more hydrogen atoms on the alkoxy is or are replaced by a fluoro group.

"Fluoroalkyl" means an alkyl group as defined above wherein one or more hydrogen atoms on the alkyl are replaced by a fluoro group.

"Halo" means fluoro, chloro, bromo, or iodo groups. Preferred are fluoro, chloro or bromo, and more preferred are fluoro and chloro.

"Halogen" means fluorine, chlorine, bromine, or iodine. Preferred are fluorine, chlorine and bromine.

"Heteroalkyl" is a saturated or unsaturated, straight or branched, chain containing carbon and at least one heteroatom. The heteroalkyl group may, in various embodiments, have on heteroatom, or 1-2 heteroatoms, or 1-3 heteroatoms, or 1-4 heteroatoms. In one aspect the hteroalkyl chain contains from 1 to 18 (i.e., 1-18) member atoms (carbon and heteroatoms), and in various embodiments contain 1-12, or 1-6, or 1-4 member atoms. Independently, in various embodiments, the heteroalkyl group has zero branches (i.e., is a straight chain), one branch, two branches, or more than two branches. Independently, in one embodiment, the htereoalkyl group is saturated. In another embodiment, the heteroalkyl group is unsaturated. In various embodiments, the unsaturated heterolkyl may have one double bond, two double bonds, more than two double bonds, and/or one triple bond, two triple bonds, or more than two triple bonds. Heteroalkyl chains may be substituted or unsubstituted. In one embodiment, the heteroalkyl chain is unsubstituted. In another embodiment, the heteroalkyl chain is substituted. A substituted heteroalkyl chain may have 1 substituent (i.e., by monosubstituted), or may have 1-2 substituents, or 1-3 substituents, or 1-4 substituents, etc. Exemplary heteroalkyl substituents include esters (—C(O)—O—R) and carbonyls (—C(O)—).

"Heterocyclic" (or "heterocycloalkyl" or "heterocyclyl") refers to a non-aromatic saturated monocyclic or multicyclic ring system comprising 3 to 10 ring atoms (e.g., 3 to 7 ring atoms), or 5 to 10 ring atoms, in which one or more of the atoms in the ring system is an element other than carbon, for example nitrogen, oxygen or sulfur, alone or in combination. There are no adjacent oxygen and/or sulfur atoms present in the ring system. Examples of heterocyclics or heterocycloalkyls include rings having 5 to 6 ring atoms. The prefix aza, oxa or thia before the heterocyclic or heterocycloalkyl root name means that at least a nitrogen, oxygen or sulfur atom, respectively, is present as a ring atom. The nitrogen or sulfur atom of the heterocyclic or heterocycloalkyl can be optionally oxidized to the corresponding N-oxide, S-oxide or S,S-dioxide. Any nitrogen atoms may be optionally quaternized. Non-limiting examples of monocyclic heterocyclic or heterocycloalkyl rings include: piperidyl, pyrrolidinyl, piperazinyl, morpholinyl, thiomorpholinyl, thiazolidinyl, 1,3-dioxolanyl, 1,4-dioxanyl, tetrahydrofuranyl, tetrahydrothiophen-yl, and tetrahydrothiopyranyl The heterocyclyl may be unsubstituted or substituted. In one embodiment, the heterocyclyl is unsubstituted. In another embodiment, the heterocyclyl is substituted. The substituted heterocyclyl ring may contain 1 substituent, or 1-2 substituents, or 1-3 substituents, or 1-4 substituents, etc. In one embodiment, the substituents that may be present on the heterocyclyl ring are selected from acyl (—C(O)—R), alkoxy (—O—R), alkyl, aryl, alkylamino (—N(H)—R and —N(R)R), alkylthio (—S—R), amino ($—NH_2$), azido ($-N_3$), boronyl (—B(R)R or $—B(OH)_2$ or $—B(OR)_2$), carboxy (—C(O)—OH), alkoxycarbonyl (—C(O)—OR), aminocarbonyl ($—C(O)—NH_2$), aminosulfonyl ($—S(O)_2—NH_2$), alkylaminocarbonyl (—C(O)—N(H)R and —C(O)—N(R)R), cyano, halo (fluoro, bromo, chloro, iodo), haloalkyl, haloalkoxy, heterocyclyl, heteroalkyl, hydroxyl (—OH), acyloxy (—O—C(O)—R), ketone (—C(O)—R), substituted halomethylketone ($—C(O)—CH_mX_n$, where m+n=3, X=F, Cl, Br), mercapto (—SH and —S—R) and nitro ($—NO_2$) In one aspect, the R group which is, or is part of the substituent attached to the heterocyclic ring is an alkyl group having less than about 12 carbons, while in another aspect the R group is a lower alkyl group.

"Heterocycloalkylalkyl" means a heterocycloalkyl-alkyl group, wherein said heterocycloalkyl and said alkyl are as defined above, bound to a parent moiety through the alkyl group.

"Heteroaryl" means an aromatic monocyclic or multicyclic ring system comprising 5 to 14 ring atoms, or 5 to 10 ring atoms, in which one or more of the ring atoms is an element other than carbon, for example nitrogen, oxygen or sulfur, alone or in combination. Heteroaryls can contain 5 to 6 ring atoms. The prefix aza, oxa or thio before the heteroaryl root name means that at least a nitrogen, oxygen or sulfur atom respectively, is present as a ring atom. A nitrogen atom of a heteroaryl can be optionally oxidized to the corresponding N-oxide. Any nitrogen atoms may be optionally quaternized. Non-limiting examples of heteroaryls include: pyridyl, pyrazinyl, furanyl, thienyl, pyrimidinyl, isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, and benzothiazolyl. The heteroaryl may be unsubstituted or substituted. In one embodiment, the heteroaryl is unsubstituted. In another embodiment, the heteroaryl is substituted. The substituted heteroaryl ring may contain 1 substituent, or 1-2 substituents, or 1-3 substituents, or 1-4 substituents, etc. In one embodiment, the substituents that may be present on the heteroaryl ring are selected from acyl (—C(O)—R), alkoxy (—O—R), alkyl, aryl, alkylamino (—N(H)—R and —N(R)R), alkylthio (—S—R), amino ($—NH_2$), azido ($—N_3$), boronyl (—B(R)R or $—B(OH)_2$ or $—B(OR)_2$), carboxy (—C(O)—OH), alkoxycarbonyl (—C(O)—OR), aminocarbonyl ($—C(O)—NH_2$), aminosulfonyl ($—S(O)_2—NH_2$), alkylaminocarbonyl (—C(O)—N(H)R and —C(O)—N(R)R), cyano, halo (fluoro, bromo, chloro, iodo), haloalkyl, haloalkoxy, heterocyclyl, heteroalkyl, hydroxyl (—OH), acyloxy (—O—C(O)—R), ketone (—C(O)—R), substituted halomethylketone ($—C(O)—CH_mX_n$, where m+n=3, X=F, Cl, Br), mercapto (—SH and —S—R) and nitro ($—NO_2$) In one aspect, the R group which is, or is part of the substituent attached to the heteroaryl ring is an alkyl group having less than about 12 carbons, while in another aspect the R group is a lower alkyl group.

"Heteroaralkyl" or "heteroarylalkyl" means a heteroaryl-alkyl-group, in which the heteroaryl and alkyl are as previously described. Preferred heteroaralkyls can contain a lower alkyl group. Non-limiting examples of suitable aralkyl groups include pyridylmethyl, 2-(furan-3-yl)ethyl and quinolin-3-ylmethyl. The bond to the parent moiety is through the alkyl.

"Hydroxyalkyl" means an HO-alkyl-group, in which alkyl is previously defined. Preferred hydroxyalkyls contain lower alkyl. Non-limiting examples of suitable hydroxyalkyl groups include hydroxymethyl and 2-hydroxyethyl.

"Hydrate" is a solvate wherein the solvent molecule is $H_2O$.

"Solvate" means a physical association of a compound of this disclosure with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like.

The term "substituted" means substitution with specified groups other than hydrogen, or with one or more groups, moieties or radicals which can be the same or different, with each, for example, being independently selected.

When $R^3$ is an ionized carboxylate the structure of $R^3$ is $—(CH_2)_n—COO^-$, when $R^3$ is an amine the structure is $—(CH_2)_n—N^+(R^{10})_3$ where $R^{10}$ is independently alkyl, lower alkyl, and hydrogen; when $R^3$ is a phosphonate the structure is $—(CH_2)_n—PO(OH)_2$, in either its monobasic or dibasic ionization state; when $R_3$ is a phosphate the structure is $—(CH_2)_n—O—PO(OH)_2$, in either its monobasic or dibasic ionization state. Wherein n is an integer from 1 to 5. Therefore, each ionized carboxylate, amine, phosphonate or phosphate forms a salt.

Examples of "disease modifying antirheumatic drugs" (i.e., DMARDs) include, for example, methotrexate, aminopterin, sulfasalzine, leflunomide, TNFa directed agents (e.g., infliximab, etanercept, and adalimumab), IL-1 directed agents (e.g., anakinra) B cell directed agents (e.g., rituximab), T cell directed agents (e.g., alefacept, efalizumab, and CTLA4-1g), TNFa-converting enzyme inhibitors, interleukin-1 converting enzyme is inhibitors, and p38 kinase inhibitors.

The term "other classes of compounds indicated for the treatment of rheumatoid arthritis", as used herein, unless indicated otherwise, means: compounds selected from the group consisting of: IL-1 directed agents (e.g., anakinra); B cell directed agents (e.g., rituximab); T cell directed agents (e.g., alefacept, efalizumab, and CTLA4-1g), TNFa-converting enzyme inhibitors, interleukin-1 converting enzyme inhibitors, and p38 kinase inhibitors.

The compounds of formula (1) and formula (2) form salts that are also within the scope of this disclosure. Reference to a compound of formula (1) or formula (2) herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of formula (1) or formula (2) contains both a basic moiety, such as, but not limited to a pyridine or imidazole, and an acidic moiety, such as, but not limited to a carboxylic acid, zwitterions ("inner salts") may be formed and are included within the term "salt(s)" as used herein. The salts can be pharmaceutically acceptable (i.e., non-toxic, physiologically acceptable) salts, although other salts are also useful. Salts of the compounds of the formula (1) or formula (2) may be formed, for example, by reacting a compound of formula (1) or formula (2) with an amount of acid or base, such as an equivalent amount, in a medium such as one in which the salt precipitates or in an aqueous medium followed by lyophilization.

Exemplary acid addition salts include acetates, adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides, hydrobromides, hydroiodides, 2-hydroxyethanesulfonates, lactates, maleates, methanesulfonates, 2-napthalenesulfonates, nicotinates, nitrates, oxalates, pectinates, persulfates, 3-phenylpropionates, phosphates, picrates, pivalates, propionates, salicylates, succinates, sulfates, sulfonates (such as those mentioned herein), tartarates, thiocyanates, toluenesulfonates (also known as tosylates) undecanoates, and the like. Additionally, acids which are generally considered suitable for the formation of pharmaceutically useful salts from basic pharmaceutical compounds are discussed, for example, by S. Berge et al, J. Pharmaceutical Sciences (1977) 66(1)1-19; P. Gould, International J. Pharmaceutics (1986) 33 201-217; Anderson et al, The Practice of Medicinal Chemistry (1996), Academic Press, New York; and in The Orange Book (Food & Drug Administration, Washington, D.C. on their website). These disclosures are incorporated herein by reference herein.

Exemplary basic salts include ammonium salts, alkali metal salts such as sodium, lithium, and potassium salts, alkaline earth metal salts such as calcium and magnesium salts, salts with organic bases (for example, organic amines) such as benzathines, dicyclohexylamines, hydrabamines (formed with N,N-bis(dehydroabietyl)ethylenediamine), N-methyl-D-glucamines, N-methyl-D-glucamides, t-butyl amines, and salts with amino acids such as arginine, lysine and the like. Basic nitrogen-containing groups may be quarternized with agents such as lower alkyl halides (e.g., methyl, ethyl, propyl, and butyl chlorides, bromides and iodides), dialkyl sulfates (e.g., dimethyl, diethyl, dibutyl, and diamyl sulfates), long chain halides (e.g., decyl, lauryl, myristyl, and stearyl chlorides, bromides and iodides), arylalkyl halides (e.g., benzyl and phenethyl bromides), and others.

All such acid and base salts are intended to be pharmaceutically acceptable salts within the scope of the disclosure and all acid and base salts are considered equivalent to the free forms of the corresponding compounds for purposes of the disclosure.

Compounds of formula (1) or formula (2) can exist in unsolvated and solvated forms, including hydrated forms. In general, the solvated forms, with pharmaceutically acceptable solvents such as water, ethanol and the like, are equivalent to the unsolvated forms for the purposes of this disclosure.

Compounds of formula (1) or formula (2) and salts, solvates and prodrugs thereof, may exist in their tautomeric form (for example, as an amide or imino ether). All such tautomeric forms are contemplated herein as part of the present disclosure.

Also within the scope of the present disclosure are polymorphs of the compounds of this disclosure (i.e., polymorphs of the compounds of formula 1 are within the scope of this disclosure).

Prodrugs of the compounds of formula (1) or formula (2) or pharmaceutically acceptable salts or solvates thereof are within the scope of this disclosure.

All stereoisomers (for example, geometric isomers, optical isomers and the like) of the present compounds (including those of the salts, solvates and prodrugs of the compounds as well as the salts and solvates of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this disclosure. Individual stereoisomers of the compounds of this disclosure may, for example, be substantially free of other isomers, or may be admixed, for example, as racemates or with all other, or other selected, stereoisomers. The chiral centers of the compounds herein can have the S or R configuration as defined by the IUPAC 1974 Recommendations. The use of the terms "salt", "solvate", "prodrug" and the like, is intended to equally apply to the salt, solvate and prodrug of enantiomers, stereoisomers, rotamers, tautomers, racemates or prodrugs of the disclosed compounds.

Classes of compounds that can be used as the chemotherapeutic agent (antineoplastic agent) include: alkylating agents, antimetabolites, natural products and their derivatives, hormones and steroids (including synthetic analogs), and synthetics. Examples of compounds within these classes are given below.

Alkylating agents (including nitrogen mustards, ethylenimine derivatives, alkyl sulfonates, nitrosoureas and triazenes): [Uracil mustard, Chlormethine, Cyclophosphamide, Ifosfamide, Melphalan, Chlorambucil, Pipobroman, Triethylene-melamine, Triethylenethiophos-phoramine, Busulfan, Carmustine, Lomustine, Streptozocin, Dacarbazine, and Temozolomide] *uracil mustard, chlormethine, cyclophosphamide, ifosfamide, melphalan, chlorambucil, pipobroman, triethylene-melamine, triethylenethiophosphoramine, busulfan, carmustine, lomustine, streptozocin, dacarbazine, and temozolomide.*

Antimetabolites (including folic acid antagonists, pyrimidine analogs, purine analogs and adenosine deaminase inhibitors): [Methotrexate, Aminopterin, 5-Fluorouracil, Floxuridine, Cytarabine, 6-Mercaptopurine, 6-Thioguanine, Fludarabine phosphate, Pentostatine, and Gemcitabine] *methotrexate, aminopterin, 5-fluorouracil, floxuridine, cytarabine, 6-mercaptopurine, 6-thioguanine, fludarabine phosphate, pentostatine, and gemcitabine.*

Natural products and their derivatives (including vinca alkaloids, antitumor antibiotics, enzymes, lymphokines and epipodophyllotoxins): [Vinblastine, Vincristine, Vindesine, Bleomycin, Dactinomycin, Daunorubicin, Doxorubicin, Epirubicin, Idarubicin, paclitaxel (Taxol®), Mithramycin, Deoxycoformycin, Mitomycin-C, L-Asparaginase, Interferons (especially IFN-), etoposide, and Teniposide] *vinblastine, vincristine, vindesine, bleomycin, dactinomycin, daunorubicin, doxorubicin, epirubicin, idarubicin, paclitaxel (TAXOL®), mithramycin, deoxycoformycin, mitomycin-C, L-asparaginase, interferons (especially IFN-β), etoposide, and teniposide.*

Hormones and steroids (including synthetic analogs): [17β-Ethinylestradiol, Diethylstilbestrol, Testosterone, Prednisone, Fluoxymesterone, Dromostanolone propionate, Testolactone, Megestrolacetate, Tamoxifen, Methylprednisolone, Methyltestosterone, Prednisolone, Triamcinolone, Chlorotrianisene, Hydroxyprogesterone, Aminoglutethimide, Estramustine, Medroxyprogesteroneacetate, Leuprolide, Flutamide, Toremifene, Zoladex] *17β-ethinylestradiol, diethylstilbestrol, testosterone, prednisone, fluoxymesterone, dromostanolone propionate, testolactone, megestrolacetate, tamoxifen, methylprednisolone, methyltestosterone, prednisolone, triamcinolone, chlorotrianisene, hydroxyprogesterone, aminoglutethimide, estramustine, medroxyprogesteroneacetate, leuprolide, flutamide, toremifene, and ZOLADEX®.*

Synthetics (including inorganic complexes such as platinum coordination complexes): [Cisplatin, Carboplatin, Hydroxyurea, Amsacrine, Procarbazine, Mitotane, Mitoxantrone, Levamisole, and Hexamethylmelamine] *cisplatin, carboplatin, hydroxyurea, amsacrine, procarbazine, mitotane, mitoxantrone, levamisole, and hexamethylmelamine.*

Methods for the safe and effective administration of most of these chemotherapeutic agents are known to those skilled in the art. In addition, their administration is described in the standard literature. For example, the administration of many of the chemotherapeutic agents is described in the "Physicians' Desk Reference" (PDR), e.g., 2008 edition (Thomson P D R, Montvale, N.J. 07645-1742, 25 USA); the disclosure of which is incorporated herein by reference herein.

As used herein, a microtubule affecting agent is a compound that interferes with cellular mitosis, i.e., having an anti-mitotic effect, by affecting microtubule formation and/or action. Such agents can be, for instance, microtubule stabilizing agents or agents that disrupt microtubule formation.

Microtubule affecting agents useful in this disclosure are well known to those of skilled in the art and include, but are not limited to allocolchicine (NSC 406042), Halichondrin B (NSC 609395), colchicine (NSC 757), colchicine derivatives (e.g., NSC 33410), dolastatin 10 (NSC 376128), maytansine (NSC 153858), rhizoxin (NSC 332598), paclitaxel (Taxol, NSC 125973), Taxol derivatives (e.g., derivatives (e.g., NSC 608832), thiocolchicine (NSC 361792), trityl cysteine (NSC 83265), vinblastine sulfate (NSC 49842), vincristine sulfate (NSC 67574), epothilone A, epothilone, and discodermolide (see Service, (1996) Science, 274:2009) estramustine, nocodazole, MAP4, and the like. Examples of such agents are also described in the scientific and patent literature, see, e.g., Bulinski (1997) J. Cell Sci. 110:3055-3064; Panda (1997) Proc. Natl. Acad. Sci. USA 94:10560-10564; Muhlradt (1997) Cancer Res. 57,3344-3346; Nicolaou (1997) Nature 387:268-272; Vasquez (1997) Mol. Biol. Cell. 8:973-985; Panda (1996) J. Biol. Chem. 271:29807-29812.

Particularly, agents can be compounds with paclitaxel-like activity. These include, but are not limited to paclitaxel and paclitaxel derivatives (paclitaxel-like compounds) and analogues. Paclitaxel and its derivatives are available commercially. In addition, methods of making paclitaxel and paclitaxel derivatives and analogues are well known to those of skilled in the art (see, e.g., U.S. Pat. Nos. 5,569,729; 5,565,478; 5,530,020; 5,527,924; 5,508,447; 5,489,589; 5,488,116; 5,484,809; 5,478,854; 5,478,736; 5,475,120; 5,468,769; 5,461,169; 5,440,057; 5,422,364; 5,411,984; 5,405,972; and 5,296,506, the disclosures of which are incorporated by reference herein).

Additional microtubule affecting agents can be assessed using one of many such assays known in the art, e.g., a semiautomated assay which measures the tubulin-polymerizing activity of paclitaxel analogs in combination with a cellular assay to measure the potential of these compounds to block cells in mitosis (see Lopes (1997) Cancer Chemother. Pharmacol. 41:37-47).

Therapeutic Activity

Modulators of neutrophil activity can have great therapeutic benefit in a number of indications. In disease states characterized by an improperly heightened neutrophil response, an inhibitor of neutrophil activity would be indicated. In patients suffering from, for example neutropenia, a neutrophil agonist or activator has clinical benefit.

Preparation of the Compounds

It is understood that in the following description, combinations of substituents and/or variables of the depicted formulae are permissible only if such contributions result in stable compounds.

It will also be appreciated by those skilled in the art that in the processes described below the functional groups of intermediate compounds may need to be protected by suitable protecting groups. Such functional groups include amino, boronic acid, hydroxyl, mercapto and carboxylic acid. Suitable protecting groups for amino, amidino, and guanidine include t-butoxycarbonyl, benzyloxycarbonyl, 9-fluorenylmethoxycarbonyl, and the like. Suitable boronic acid protecting groups include pinacol esters, pinanediol esters, N-methyliminodiacetic acid (MIDA) esters, trifluoroborate salt, and the like. Suitable hydroxyl protecting groups include trialkylsilyl or diarylsilyl ethers (e.g., trimethylsilyl, t-butyldimethylsilyl, or t-butyldiphenylsilyl), trityl ethers, benzyl ethers and the like. Suitable protecting groups for mercapto include thioethers (e.g. S-benzyl, S-p-nitrobenzyl, S-9-fluorenylmethyl, S-trityl), thioesters —C(O)—R (where R is alkyl, aryl or arylalkyl), and the like. Suitable protecting groups for carboxylic acid include alkyl, aryl, or arylalkyl esters.

Compounds of the present invention may be prepared from readily available starting materials according to methods set forth in the synthetic schemes below.

Scheme 1

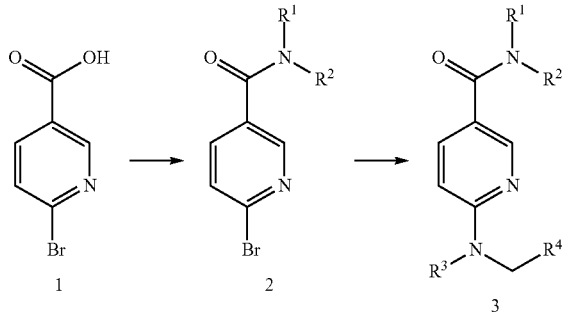

As illustrated above, 6-bromonicotinic acid (compound 1) can be amidated with a variety of primary and secondary amines to yield either mono- or di-substituted pyridinecarboxamide as represented by compound 2. Suitable reaction conditions using peptide coupling reagents are known in the art, and include the use of EEDQ, DCCI, mixed carbonic anhydrides and phosphonium coupling reagents such as PyBOP and PyBrOP. The halogen substituent of compound 2 is then displaced by the nitrogen of either primary or secondary amines to yield compound 3. This alkylation reaction is base catalyzed, and is typically run in a suitable solvent, e.g. DMF with a suitable base, e.g. triethylamine. Alternatively, phase transfer catalyzed conditions (e.g. potassium tert-butoxide, 18-crown-6 ether in toluene) can be used to effect this alkylation.

Scheme 2

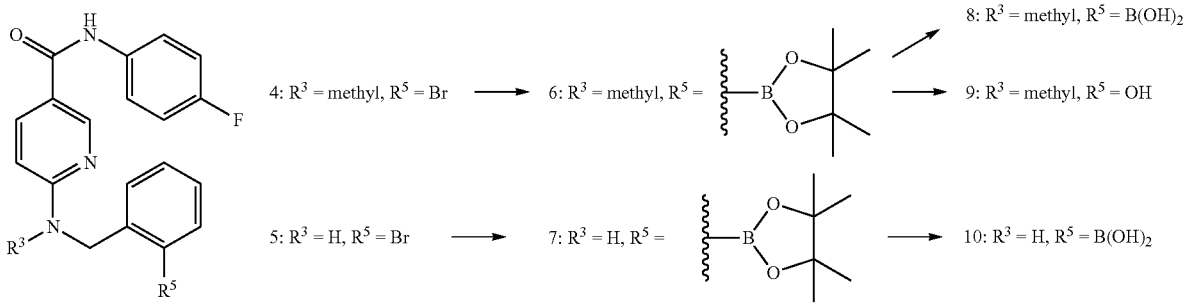

In the preparation of compounds 4 and 5, N-methyl-2-bromo-benzylamine and 2-bromo-benzylamine were used, respectively (Scheme 2). The boronic acid moieties were added via palladium catalyzed insertion reaction as pinacol boronate esters. The pinacol esters can be removed by treatment with $KHF_2$, and the boronic acid moiety can be replaced with a hydroxyl group through oxidation with a suitable reagent, e.g. Oxone® (from Webb, K. S. and Levy, D, Tetrahedron Letters 36:5117-5118, 1995) or peroxide.

Scheme 3

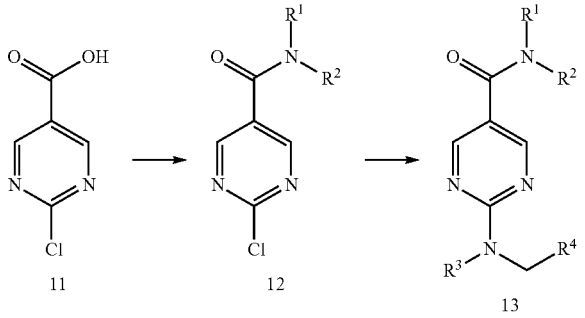

As illustrated above, 2-chloropyrimidine-5-carboxylic acid (compound 11) can be amidated with a variety of primary and secondary amines to yield either mono- or di-substituted pyrimidinecarboxamide as represented by compound 12. Suitable reaction conditions using peptide coupling reagents are known in the art, and include, for example, the use of EEDQ, DCCI, mixed carbonic anhydrides and phosphonium coupling reagents such as PyBOP and PyBrOP. The halogen substituent of compound 12 is then displaced by the nitrogen of either primary or secondary amines to yield compound 13. This alkylation reaction is base catalyzed, and is typically run in a suitable solvent, e.g. DMF with a suitable base, e.g. triethylamine. Alternatively, phase transfer catalyzed conditions (e.g., potassium tert-butoxide, 18-crown-6 ether in toluene) can be used to effect this alkylation.

Scheme 4

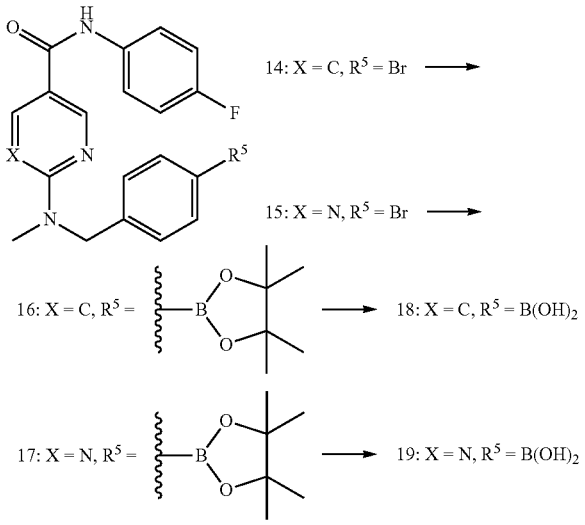

In the preparation of compounds 14 and 15, N-methyl-4-bromo-benzylamine was reacted with compounds 2 and 12, respectively, where $R^1$ is H, and $R^2$ is 4-fluorophenyl (Scheme 4). The boronic acid moieties were added via palladium catalyzed insertion reaction as pinacol boronate esters. The pinacol esters can be removed by treatment with $KHF_2$, and the boronic acid moiety can be replaced with a hydroxyl group through oxidation with a suitable reagent, e.g. Oxone® (from Webb, K. S. and Levy, D, Tetrahedron Letters 36:5117-5118, 1995) or peroxide.

Methods of Treatment

One embodiment is directed to a pharmaceutical composition comprising at least one compound of formula (1) or formula (2), or a pharmaceutically acceptable salt or solvate thereof, in combination with a pharmaceutically acceptable carrier.

The methods of treatment of this disclosure are advantageous in treating diseases where the ELR-CXC chemokine binds to CXCR2. Another embodiment of the disclosure is directed to a method of treating CXCR2 chemokine mediated diseases in a patient in need of such treatment comprising administering to the patient a therapeutically effective amount of at least one compound of formula (1) or formula (2), or a pharmaceutically acceptable salt or solvate thereof.

Another embodiment of the disclosure is a method of treating CXCR2 chemokine mediated diseases in a patient in need thereof comprises administering to the patient (a) an effective amount of at least one compound of formula (1) or formula (2), or a pharmaceutically acceptable salt or solvate thereof, concurrently or sequentially with (b) at least one additional agent, drug, medicament, antibody and/or inhibitor useful for the treatment of CXCR2 chemokine mediated diseases. Examples of the additional medicament, drug or agent include, but are not limited to, disease modifying antirheumatic drugs; nonsteroidal antiinflammatory drugs (NSAIDs); COX-2 selective inhibitors; COX-1 inhibitors; immunosuppressives; steroids; biological response modifiers; and other anti-inflammatory agents or therapeutics useful for the treatment of CXCR2 chemokine mediated diseases.

Another embodiment of the method of treating a CXCR2 chemokine mediated disease is administering (a) a therapeutically effective amount of at least one compound of formula (1) or formula (2), or a pharmaceutically acceptable salt or solvate thereof, concurrently or sequentially with (b) at least one medicament selected from the group consisting of: disease modifying antirheumatic drugs; nonsteroidal anti-inflammatory drugs; COX-2 selective inhibitors; COX-1 inhibitors; immunosuppressives; steroids; biological response modifiers; and other anti-inflammatory agents or therapeutics useful for the treatment of CXCR1 and/or CXCR2 chemokine mediated diseases.

Another embodiment of this disclosure is a method for treating cancer in a patient in need of such treatment, the method comprises administering to said patient a therapeutically effective amount of a compound of formula (1) or formula (2), or a pharmaceutically acceptable salt or solvate thereof. Another embodiment of this disclosure is a method for treating cancer comprising administering to the patient a therapeutic amount of at least one compound of formula (1) or formula (2), or a pharmaceutically acceptable salt or solvate thereof, concurrently or sequentially with (a) at least one antineoplastic agent selected from the group consisting of: (1) gemcitabine, (2) paclitaxel, (3) 5-Fluorouracil (5-FU), (4) cyclo-phosphamide, (5) temozolomide and (6) Vincristine or (b) at least one agent selected from the group consisting of (1) microtubule affecting agents, (2) antineoplastic agents, (3) anti-angiogenesis agents, (4) VEGF receptor kinase inhibitors, (5) antibodies against the VEGF receptor, (6) interferon, and (7) radiation.

Another embodiment of this disclosure is a method for treating asthma in a patient in need of such treatment the method comprising administering to the patient a therapeutically effective amount of at least one compound of formula (1) or formula (2), or a pharmaceutically acceptable salt or solvate thereof. Another embodiment of this disclosure is a method for treating a pulmonary disease (e.g., COPD, asthma, or cystic fibrosis), in a patient in need of such treatment, the method comprising administering to the patient a therapeutically effective amount of: (a) at least one compound of formula (1) or formula (2), or a pharmaceutically acceptable salt or solvate thereof, concurrently or sequentially with (b) at least one compound selected from the group consisting of: glucocorticoids, 5-lipoxygenase inhibitors, beta-2 adrenoceptor agonists, muscarinic M1 antagonists, muscarinic M3 antagonists, muscarinic M2 agonists, NK3 antagonists, LTB4 antagonists, cysteinyl leukotriene antagonists, bronchodilators, PDE4 inhibitors, PDE inhibitors, elastase inhibitors, MMP inhibitors, phospholipase A2 inhibitors, phospholipase D inhibitors, histamine H1 antagonists, histamine H3 antagonists, dopamine agonists, adenosine A2 agonists, NK1 and NK2 antagonists, GABA-β agonists, nociceptin agonists, expectorants, mucolytic agents, decongestants, antioxidants, anti-IL-8 antibodies, anti-IL-5 antibodies, anti-IgE antibodies, anti-TNF antibodies, IL-10, adhesion molecule inhibitors, and growth hormones.

Another embodiment of this disclosure is a method for treating multiple sclerosis, comprising administering to the patient:(a) a therapeutically effective amount of at least one compound of formula (1) or formula (2), or a pharmaceutically acceptable salt or solvate thereof, concurrently or sequentially with (b) a therapeutically effective amount of at least one compound selected from the group consisting of: glatiramer acetate, glucocorticoids, methotrexate, azothioprine, mitoxantrone, and CB2-selective inhibitors.

Another embodiment of this disclosure is a method of treating multiple sclerosis comprising concurrent or sequential administration of a therapeutically effective amount of: (a) at least one compound of formula (1) or formula (2), or a pharmaceutically acceptable salt or solvate thereof, and (b) at least one compound selected from the group consisting of: methotrexate, cyclosporin, leflunimide, sulfasalazine, β-methasone, β-interferon, glatiramer acetate, prednisone, etonercept, and infliximab.

Another embodiment of this disclosure is a method for treating rheumatoid arthritis in a patient in need of such treatment comprising administering to said patient a therapeutically effective amount of at least one compound of formula 1, or a pharmaceutically acceptable salt or solvate thereof.

Another embodiment of this disclosure is a method for treating rheumatoid arthritis in a patient in need of such treatment comprising administering to said patient a therapeutically effective amount of at least one compound of formula (1) or formula (2), or a pharmaceutically acceptable salt or solvate thereof, in combination with at least one compound selected from the group consisting of COX-2 inhibitors, COX-1 inhibitors, immunosuppressives (e.g., methotrexate, aminopterin, cyclosporin, leflunimide and sulfasalazine), steroids (e.g., betamethasone, cortisone and dexamethasone), PDE 4 inhibitors, anti-TNF-α compounds, MMP inhibitors, glucocorticoids, chemokine inhibitors, CB2-selective agents, and other classes of compounds indicated for the treatment of rheumatoid arthritis.

Another embodiment of this disclosure is a method for treating stroke and ischemia reperfusion injury in a patient in need of such treatment the method comprising administering to the patient a therapeutically effective amount of: (a) at least one compound of formula (1) or formula (2), or a pharmaceutically acceptable salt or solvate thereof, concurrently or sequentially with (b) at least one compound selected from the group consisting of: thrombolitics (e.g., tenecteplase, TPA, alteplase), antiplatelet agents (e.g., gpllb/llla), antagonists (e.g., abciximab and eftiifbatide), anticoagulants (e.g., heparin), and other compounds indicated for the treatment of rheumatoid arthritis.

Another embodiment of this disclosure is a method for treating stroke and ischemia reperfusion injury in a patient in need of such treatment the method comprising administering to the patient a therapeutically effective amount of: (a) at least one compound of formula (1) or formula (2), or a pharmaceutically acceptable salt or solvate thereof concurrently or sequentially with (b) at least one compound selected from the group consisting of: tenecteplase, TPA, alteplase, abciximab, eftiifbatide, and heparin.

Another embodiment of this disclosure is a method for treating psoriasis in a patient in need of such treatment, the method comprising administering to the patient a therapeutically effective amount of: a) at least one compound of formula (1) or formula (2), or a pharmaceutically acceptable salt or solvate thereof, concurrently or sequentially with (b) at least one compound selected from the group consisting of: immunosuppressives (e.g., methotrexate, aminopterin, cyclosporin, efalizumab, alefacept, leflunimide and sulfasalazine), steroids (e.g., β-methasone) and anti-TNFα compounds (e.g., etonercept and infliximab).

This disclosure also provides a method for treating CXCR2 mediated disease or condition selected from the group consisting of: pain (e.g., acute pain, acute inflammatory pain, chronic inflammatory pain, and neuropathic pain), acute inflammation, chronic inflammation, rheumatoid arthritis, psoriasis, atopic dermatitis, asthma, bronchopulmonary dysplasia, COPD, adult respiratory disease, arthritis, inflammatory bowel disease, Crohn's disease, ulcerative colitis, septic shock, endotoxic shock, gram negative sepsis, toxic shock syndrome, stroke, ischemia reperfusion injury, renal reperfusion injury, glomerulonephritis, thrombosis, Alzheimer's disease, graft vs. host reaction (i.e., graft-versus-host disease), allograft rejections (e.g., acute allograft rejection, and chronic allograft rejection), malaria, acute respiratory distress syndrome, delayed type hypersensitivity reaction, atherosclerosis, cerebral ischemia, cardiac ischemia, osteoarthritis, multiple sclerosis, restinosis, angiogenesis, angiogenesis associated with tumor growth, osteoporosis, gingivitis, respiratory viruses, herpes viruses, hepatitis viruses, HIV, Kaposi's sarcoma associated virus (i.e., Kaposi's sarcoma), meningitis, cystic fibrosis, pre-term labor, cough, pruritis, multi-organ dysfunction, trauma, strains, sprains, contusions, psoriatic arthritis, herpes, encephalitis, CNS vasculitis, traumatic brain injury, systemic tumors, CNS tumors, tumors dependent on angiogenesis for growth, leukopenia and neutropenia, chemotherapy-induced leukopenia and neutropenia, opportunistic infections associated with neutropenia or leukopenia, subarachnoid hemorrhage, post surgical trauma, interstitial pneumonitis, hypersensitivity, crystal induced arthritis, acute pancreatitis, chronic pancreatitis, acute alcoholic hepatitis, necrotizing enterocolitis, chronic sinusitis, angiogenic ocular disease, ocular inflammation, retinopathy of prematurity, diabetic retinopathy, macular degeneration with the wet type preferred, corneal neovascularization, polymyositis, vasculitis, acne, gastric ulcers, duodenal ulcers, celiac disease, esophagitis, glossitis, airflow obstruction, airway hyperresponsiveness (i.e., airway hyperreactivity), bronchiectasis, bronchiolitis, bronchiolitis obliterans, chronic bronchitis, cor pulmonae, dyspnea, emphysema, hypercapnea, hyperinflation, hypoxemia, hyperoxia-induced inflammations, hypoxia, surgical lung volume reduction, pulmonary fibrosis, pulmonary hypertension, right ventricular hypertrophy, peritonitis associated with continuous ambulatory peritoneal dialysis (CAPD), granulocytic ehrlichiosis, sarcoidosis, small airway disease, ventilation-perfusion mismatching, wheeze, colds, gout, alcoholic liver disease, lupus, burn therapy (i.e., the treatment of burns), periodontitis, cancer, transplant reperfusion injury, early transplantation rejection (e.g., acute allograft rejection) in a patient in need of such treatment comprising administering to said patient an effective amount of at least one compound of formula (1) or formula (2), or a pharmaceutically acceptable salt or solvate thereof.

Another embodiment of this disclosure is a method for treating diseases such as allograft rejections, early transplantation rejections, autoimmune deafness, myocarditis, neuropathies, autoimmune diseases and vasculitis syndromes wherein said:

(a) allograft rejections are selected from the group consisting of acute allograft rejections and chronic allograft rejections;

(b) early transplantation rejection is an acute allograft rejection;

(c) autoimmune deafness is Meniere's disease;

(d) myocarditis is viral myocarditis;

(e) neuropathies are selected from the group consisting of IgA neuropathy, membranous neuropathy and idiopathic neuropathy;

(f) autoimmune diseases are anemias; and (g) vasculitis syndromes are selected from the group consisting of giant cell arteries, Behcet's disease and Wegener's granulomatosis.

Another embodiment of this disclosure is a method for treating COPD in a patient in need of such treatment comprising administering to said patient a therapeutically effective amount of at least one (usually one) compound of formula (1) or formula (2), or a pharmaceutically acceptable salt or solvate thereof.

Another embodiment of this disclosure is a method for treating arthritis in a patient in need of such treatment comprising administering to said patient a therapeutically effective amount of at least one compound of formula (1) or formula (2), or a pharmaceutically acceptable salt or solvate thereof.

Another embodiment of this disclosure is a method for treating osteoarthritis in a patient in need of such treatment comprising administering to said patient a therapeutically effective amount of at least one compound of formula (1) or formula (2), or a pharmaceutically acceptable salt or solvate thereof.

Another embodiment of this disclosure is a method for treating pain in a patient in need of such treatment comprising administering to said patient a therapeutically effective amount of at least one compound of formula (1) or formula (2), or a pharmaceutically acceptable salt or solvate thereof.

Another embodiment of this disclosure is a method for treating pain in a patient in need of such treatment comprising administering to said patient a therapeutically effective amount of at least one compound of formula (1) or formula (2), or a pharmaceutically acceptable salt or solvate thereof, and administering a therapeutically effective amount of at least one medicament selected from the group consisting of: NSAIDs, COXIB inhibitors (e.g., COX-1 and COX-2 inhibitors), anti-depressants, and anti-convulsants.

Another embodiment of this disclosure is a method for treating acute pain in a patient in need of such treatment comprising administering to said patient a therapeutically effective amount of at least one (usually one) compound of formula (1) or formula (2), or a pharmaceutically acceptable salt or solvate thereof.

Another embodiment of this disclosure is a method for treating acute inflammatory pain in a patient in need of such treatment comprising administering to said patient a therapeutically effective amount of at least one compound of formula (1) or formula (2), or a pharmaceutically acceptable salt or solvate thereof.

Another embodiment of this disclosure is a method for treating chronic inflammatory pain in a patient in need of such treatment comprising administering to said-patient a therapeutically effective amount of at least one compound of formula (1) or formula (2), or a pharmaceutically acceptable salt or solvate thereof.

Another embodiment of this disclosure is a method for treating neuropathic pain in a patient in need of such treatment comprising administering to said patient a therapeutically effective amount of at least one compound of formula (1) or formula (2), or a pharmaceutically acceptable salt or solvate thereof.

Another embodiment of this disclosure is a pharmaceutical composition comprising at least one compound of formula (1) or formula (2), or a pharmaceutically acceptable salt or solvate thereof, and at least one other agent, medicament, antibody and/or inhibitor disclosed above, and a pharmaceutically acceptable carrier.

In general the compounds used to treat pain will have CXCR2 antagonistic activity.

NSAIDs are well known to those skilled in the art and can be used in their known dosages and dosage regimens. Examples of NSAIDs include but are not limited to: piroxicam, ketoprofen, naproxen, indomethacin, and ibuprofen COXIB inhibitors are well known to those skilled in the art and can be used in their known dosages and dosage regimens. Examples of COXIB inhibitors include, but are not limited to: rofecoxib and celecoxib. Anti-depressants are well known to those skilled in the art and can be used in their known dosages and dosage regimens. Examples of anti-depressants include but are not limited to: amitriptyline and nortriptyline. Anti-convulsants are well known to those skilled in the art and can be used in their known dosages and dosage regimens. Examples of anti-convulsants include but are not limited to: gabapentin, carbamazepine, pregabalin, and lamotragine.

Pharmaceutical Compositions

For preparing pharmaceutical compositions from the compounds described by this disclosure, inert, pharmaceutically acceptable carriers can be either solid or liquid. Solid form preparations include powders, tablets, dispersible granules, capsules, cachets and suppositories. The powders and tablets may be comprised of from about 5 to about 95 percent active ingredient. Suitable solid carriers are known in the art, e.g., magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), Remington: The Science and Practice of Pharmacy, 20th Edition, (2000), Lippincott Williams & Wilkins, Baltimore, Md. which is incorporated herein by reference.

Liquid form preparations include solutions, suspensions and emulsions. As an example may be mentioned water or water-propylene glycol solutions for parenteral injection or addition of sweeteners and opacifiers for oral solutions, suspensions and emulsions. Liquid form preparations may also include solutions for intranasal administration. Liquid form preparations may also include dissolution in lipid-based, self-emulsifying drug delivery systems (SEDDS) such as Labrasol® or Gelucire® for oral administration.

Aerosol preparations suitable for inhalation may include solutions and solids in powder form, which may be in combination with a pharmaceutically acceptable carrier, such as an inert compressed gas, e.g. nitrogen.

Also included are solid form preparations which are intended to be converted, shortly before use, to liquid form preparations for either oral or parenteral administration. Such liquid forms include solutions, suspensions and emulsions.

The compounds of this disclosure may also be deliverable transdermally. The tansdermal composition can take the form of creams, lotions, aerosols and/or emulsions and can be included in a transdermal patch of the matrix or reservoir type as are conventional in the art for this purpose.

The compound can be administered orally.

A suitable pharmaceutical preparation is in a unit dosage form. In such form, the preparation is subdivided into suitably sized unit doses containing appropriate quantities of the active component, e.g., an effective amount to achieve the desired purpose.

The quantity of active compound in a unit dose of preparation may be varied or adjusted from about 0.01 mg to about 1000 mg, or from about 0.01 mg to about 750 mg, or from about 0.01 mg to about 500 mg, or from about 0.01 mg to about 250 mg, according to the particular application.

The actual dosage employed may be varied depending upon the requirements of the patient and the severity of the condition being treated. Determination of the proper dosage regimen for a particular situation is within the skill of the art. For convenience, the total dosage may be divided and administered in portions during the day as required.

The amount and frequency of administration of the compounds of this disclosure and/or the pharmaceutically acceptable salts thereof will be regulated according to the judgment of the attending clinician considering such factors as age, condition and size of the patient as well as severity of the symptoms being treated. A typical recommended daily dosage regimen for oral administration can range from about 0.04 mg/day to about 4000 mg/day, in two to four divided doses.

The amount and frequency of administration of the compounds of either formula (1) or formula (2) and the chemotherapeutic agents and/or radiation therapy will be regulated according to the judgment of the attending clinician (physician) considering such factors as age, condition and size of the patient as well as severity of the disease being treated. A dosage regimen of the compound of either formula (1) or formula (2) can be oral administration of from 10 mg to 2000 mg/day, or 10 to 1000 mg/day, or 50 to 600 mg/day, in two to four (or two) divided doses, to block tumor growth. Intermittent therapy (e.g., one week out of three weeks or three out of four weeks) may also be used.

The chemotherapeutic agent and/or radiation therapy can be administered according to therapeutic protocols well known in the art. It will be apparent to those skilled in the art that the administration of the chemotherapeutic agent and/or radiation therapy can be varied depending on the disease being treated and the known effects of the chemotherapeutic agent and/or radiation therapy on that disease. Also, in accordance with the knowledge of the skilled clinician, the therapeutic protocols (e.g., dosage amounts and times of administration) can be varied in view of the observed effects of the administered therapeutic agents (i.e., antineoplastic agent or radiation) on the patient, and in view of the observed responses of the disease to the administered therapeutic agents.

If the compound of either formula (1) or formula (2), and the chemotherapeutic agent and/or radiation is not administered simultaneously or essentially simultaneously, then the initial order of administration of the compound of either formula (1) or formula (2), and the chemotherapeutic agent and/or radiation, may not be important. Thus, the compound of either formula (1) or formula (2) may be administered first, followed by the administration of the chemotherapeutic agent and/or radiation; or the chemotherapeutic agent and/or radiation may be administered first, followed by the administration of the compound of either formula (1) or formula (2). This alternate administration may be repeated during a single treatment protocol. The determination of the order of administration, and the number of repetitions of administration of each therapeutic agent during a treatment protocol, is well within the knowledge of the skilled physician after evaluation of the disease being treated and the condition of the patient.

For example, the chemotherapeutic agent and/or radiation may be administered first, especially if it is a cytotoxic agent, and then the treatment continued with the administration of the compound of either formula (1) or formula (2) followed, where determined advantageous, by the administration of the chemotherapeutic agent and/or radiation, and so on until the treatment protocol is complete.

The particular choice of a compound from either formula (1) or formula (2), and chemotherapeutic agent and/or radiation will depend upon the diagnosis of the attending physicians and their judgment of the condition of the patient and the appropriate treatment protocol.

Also, in general, the compound of either formula (1) or formula (2) and the chemotherapeutic agent do not have to be administered in the same pharmaceutical composition, and may, because of different physical and chemical characteristics, have to be administered by different routes. For example, the compound of either formula (1) or formula (2) may be administered orally to generate and maintain good blood levels thereof, while the chemotherapeutic agent may be administered intravenously. The determination of the mode of administration and the advisability of administration, where possible, in the same pharmaceutical composition, is well within the knowledge of the skilled clinician. The initial administration can be made according to established protocols known in the art, and then, based upon the observed effects, the dosage, modes of administration and times of administration can be modified by the skilled clinician.

Thus, in accordance with experience and knowledge, the practicing physician can modify each protocol for the administration of a component (therapeutic agent; i.e., the compound from either formula (1) or formula (2), chemotherapeutic agent or radiation) of the treatment according to the individual patient's needs, as the treatment proceeds.

The attending clinician, in judging whether treatment is effective at the dosage administered, will consider the general well-being of the patient as well as more definite signs such as relief of disease-related symptoms, inhibition of tumor growth, actual shrinkage of the tumor, or inhibition of metastasis. Size of the tumor can be measured by standard methods such as radiological studies, e.g., CAT or MRI scan, and successive measurements can be used to judge whether or not growth of the tumor has been retarded or even reversed. Relief of disease-related symptoms such as pain, and improvement in overall condition can also be used to help judge effectiveness of treatment.

The disclosure provided herein is exemplified by the following preparations and examples that should not be construed to limit the scope of the disclosure. Alternative mechanistic pathways and analogous structures may be apparent to those skilled in the art.

SYNTHESIS EXAMPLE 1

Preparation of Compound 2

6-Bromonicotinic acid (8.1 g, 40 mmol) was dissolved in anhydrous DMF (50 mL) under an $N_2$ atmosphere. 4-Fluoroaniline (3.9 mL, 41 mmol) and EEDQ (9.9 g, 40 mmol) were added and stirred at room temperature for 18 hours. The product was precipitated by dilution into deionized water (1.2 L), and the precipitate was filtered and washed with additional water. The product was dried under vacuum to yield 8.1 g (69%) of 2 as a white solid. ESI-MS m/z 294.9/296.9 $[M+H]^+$. Analysis: Calcd for $C_{12}H_8BrFN_2O$: C, 48.84; H, 2.73; N, 9.49. Found: C, 48.75; H, 2.57; N, 9.40. $^1H$ NMR (500 MHz, DMSO-$d_6$) δ 10.54 (s, 1H), 8.92 (d, J=2.3 Hz, 1H), 8.25-8.23 (m, 1H), 7.86-7.85 (m, 1H), 7.79 (d, J=3.8 Hz, 2H), 7.24-7.23 (m, 2H).

SYNTHESIS EXAMPLE 2

Preparation of Compound 4

Compound 2 (1.486 g, 5.04 mmol), 2-bromo-N-methylbenzylamine (0.74 mL, 5.00 mmol) and triethylamine (1.40 mL, 10.0 mmol) were dissolved in anhydrous dimethylformamide (10 mL) and placed in a pressure bottle, under an $N_2$ atmosphere. The reaction was heated to 130° C. for 2 days. The reaction was cooled to room temperature and diluted into deionized water (250 mL). The suspension was basified to pH>9 with 1 N NaOH, and extracted twice with ethyl acetate. The combined ethyl acetate extracts were dried over $Na_2SO_4$, filtered through a pad of silica gel (ethyl acetate), and dried under vacuum. The crude product was dissolved in ethyl acetate and minimal methanol and adhered to silica gel (25 g). The silica adhered compound was purified by flash silica gel chromatography (250 g silica, 3:1 hexanes:ethyl acetate) to yield 1.74 g (84%) of 4 as a white solid. ESI-MS m/z 414.1/416.1 $[M+H]^+$. Analalysis: Calcd for $C_{20}H_{17}BrFN_3O$: C, 57.98; H, 4.14; N, 10.14. Found: C, 58.08; H, 4.20; N, 10.02. $^1H$ NMR (500 MHz, DMSO-$d_6$) δ 10.06 (s, 1H), 8.69 (d, J=2.3 Hz, 1H), 8.09 (dd, J=9.0 Hz, 2.3 Hz, 1H), 7.77-7.74 (m, 2H), 7.68 (d, J=8.0 Hz, 1H), 7.33 (t, J=7.5 Hz, 1H), 7.22 (t, J=7.8 Hz, 1H), 7.18 (t, J=9.0 Hz, 2H), 6.99 (d, J=7.5 Hz, 1H), 6.78 (d, J=9.4 Hz, 1H), 4.89 (s, 2H), 3.20 (s, 3H).

SYNTHESIS EXAMPLE 3

Preparation of Compound 5

2-Bromobenzylamine hydrochloride (1.520 g, 6.83 mmol) was dissolved in water and brought to pH 12 with 1 N NaOH (15 mL). The suspension was extracted twice with ethyl acetate, and the combined ethyl acetate extracts were dried over $Na_2SO_4$, filtered, and dried under vacuum. Compound 2 (1.915 g, 6.49 mmol) was placed in a pressure bottle, and 2-bromobenzylamine (1.244 g, 6.69 mmol) was added with stirring, dissolved in N-methylpyrrolidine (13 mL), under $N_2$ atmosphere. Triethylamine (1.92 mL, 13.8 mmol) was added under $N_2$, and the bottle was heated to 130° C. for 3 days. The reaction was cooled to room temperature and added dropwise to a stirring solution of deionized water (300 mL), forming a fine precipitate. The suspension was refrigerated overnight and filtered. The crude solid was dried in a vacuum desiccator. The crude product was dissolved in tetrahydrofuran, combined with material from a previous synthesis (0.5 mmol scale), and adhered to silica gel (25 g). The combined compounds were purified by flash silica gel chromatography (250 g silica, 3:2 hexanes:ethyl acetate, then 2:1 ethyl acetate:hexanes) to yield 1.86 g (66%) of 5 as a white solid. ESI-MS m/z 400.0/402.0 $[M+H]^+$. $^1H$ NMR (500 MHz, DMSO-$d_6$) δ 9.99 (s, 1H), 8.63 (d, J=2.0 Hz, 1H), 7.96 (dd, J=8.8 Hz, 2.5 Hz, 1H), 7.79-7.74 (m, 3H), 7.65 (d, J=8.0 Hz, 1H), 7.36 (d, J=4.2 Hz, 2H), 7.24-7.20 (m, 1H), 7.17 (t, J=9.0 Hz, 2H), 6.68 (d, J=8.6 Hz, 1H), 4.61 (d, J=5.8 Hz, 2H).

SYNTHESIS EXAMPLE 4

Preparation of Compound 6

Compound 4 (1.74 g, 4.2 mmol) was dissolved in anhydrous dimethylformamide and degassed under vacuum. A pressure bottle was charged with $PdCl_2$(dppf) (255 mg, 0.312 mmol), bis(pinacolato) diboron (3.21 g, 12.6 mmol) and potassium acetate (1.22 g, 12.4 mmol), along with a stir bar. The DMF solution was added to the pressure bottle with an oven-dried pipette, rinsing with dry DMF (5 mL). The tube was sealed under nitrogen gas and heated at 80° C. for 41 hours, then cooled to room temperature. The reaction was filtered through Celite, rinsing with DMF, dried in vacu, and partitioned between water and ethyl acetate, and the aqueous layer was washed with ethyl acetate. The combined ethyl acetate layers were dried over $Na_2SO_4$, and filtered through a pad of silica gel (ethyl acetate). The filtrate was dried under vacuum to yield 4.3 g of a crude red mixture containing 6, which was used without further purification. ESI-MS (of major product) m/z 462.2 $[M+H]^+$.

SYNTHESIS EXAMPLE 5

Preparation of Compound 7

Compound 5 (201 mg, 0.50 mmol) was dissolved in anhydrous dimethylformamide and degassed under vacuum. A pressure bottle was charged with $PdCl_2$(dppf) (13 mg, 0.016 mmol), bis(pinacolato) diboron (384 mg, 1.5 mmol) and potassium acetate (150 mg, 1.5 mmol) and the solution was added under $N_2$ atmosphere. The tube was heated with stirring at 80° C. for 26 hours, then cooled to room temperature. The reaction was partitioned between water and ethyl acetate, and the aqueous layer was washed with ethyl acetate. The combined ethyl acetate layers were dried over $Na_2SO_4$, and filtered through a pad of silica gel (ethyl acetate). The filtrate was dried under vacuum, dissolved in 3:2 hexanes:ethyl acetate, and purified by flash silica gel chromatography (30 g, 3:2 hexanes:ethyl acetate) to yield 123 mg (67%) of 7 as a white foam. ESI-MS m/z 366.1 [(M-pinacol)+H]. $^1H$ NMR (500 MHz, DMSO-$d_6$) δ 9.97 (s, 1H), 8.63 (d, J=1.9 Hz, 1H), 7.93 (dd, J=8.9 Hz, 2.2 Hz, 1H), 7.76-7.74 (m, 2H), 7.71 (d, J=7.6 Hz, 1H), 7.54 (t, J=5.7 Hz, 1H), 7.42 (t, J=7.6 Hz, 1H), 7.34 (d, J=7.8 Hz, 1H), 7.26 (t, J=7.3 Hz, 1H), 7.17 (t, J=8.8 Hz, 2H), 6.61 (d, J=8.8 Hz, 1H), 4.78 (d, J=5.8 Hz, 2H), 1.31 (s, 12H). $IC_{50}$ in whole cell assay (Pharmacology Example 1)=1.5±0.3 μM.

SYNTHESIS EXAMPLE 6

Preparation of Compound 8

Crude compound 6 (4.2 mmol) was suspended with stirring in methanol (36 mL), and 4.5 M $KHF_2$ (4.0 mL, 21 mmol) was added dropwise by pipette. Additional methanol was added to rinse the walls of the flask, and the reaction was stirred at room temperature. After 2.5 hr, additional 4.5 M $KHF_2$ (8.0 mL, 42 mmol) was added to drive the reaction to completion. After stirring for another 2 hr, the reaction was diluted with methanol and dried under vacuum to yield a dark tarry substance, which was diluted with water. Sonication yielded a brown precipitate, which was isolated by vacuum filtration and dried in a vacuum desiccator to a gray solid (1.8 g). The solid was dissolved in acetonitrile (40 mL), and stirred with trimethylsilylchloride (4.8 mL, 38 mmol) and water (0.68 mL, 38 mmol) at room temperature. After stirring for about 2 hr, the reaction was quenched with saturated sodium bicarbonate (19 mL). After several minutes of stirring, the reaction was diluted with water (400 mL), and a tan solid (773 mg) was isolated by vacuum filtration and drying in a vacuum desiccator. The solid was dissolved in a mixture of ethyl acetate and methanol, adhered to silica gel (8 g), and purified by flash silica gel chromatography (80 g, step gradient of 3:2 ethyl acetate:hexanes to ethyl acetate) to yield a red foam, which was dissolved in ethyl acetate, from which 294 mg (18% from 4) of 8 precipitated as a fine white solid. ESI-MS m/z 380.1 $[M+H]^+$. $^1H$ NMR (500 MHz, DMSO-$d_6$) δ 10.03 (s, 1H), 8.70 (d, J=2.1 Hz, 1H), 8.37 (s, 2H), 8.05 (dd, J=9.1 Hz, 2.1 Hz, 1H), 7.77-7.74 (m, 2H), 7.56 (d, J=7.3 Hz, 1H), 7.30-7.26 (m, 1H), 7.22 (d, J=7.3 Hz, 1H), 7.18 (t, J=8.8 Hz, 2H), 7.03 (d, J=7.9 Hz, 1H), 6.73 (d, J=9.3 Hz, 1H), 5.00 (s, 2H), 3.19 (s, 3H). $IC_{50}$ in whole cell assay (Pharmacology Example 1)=3.7±0.6 μM.

SYNTHESIS EXAMPLE 7

Preparation of Compound 9

6-Bromonicotinamide (590 mg, 2.0 mmol), 2-(N-methylaminomethyl)phenyl boronic pinacol ester (495 mg, 2.0 mmol), potassium tert-butoxide (450 mg, 4.0 mmol), and 18-crown-6 ether (28 mg, 0.1 mmol) were suspended in anhydrous toluene under $N_2$ atmosphere and brought to reflux for 22 hours. The reaction mixture was diluted with ethyl acetate extracted twice with aqueous saturated bicarbonate. The combined saturated bicarbonate extracts were extracted twice with ethyl acetate, and the combined organic layers were washed with brine, dried over $Na_2SO_4$, filtered, and evaporated to yield 0.9 g of the crude boronate pinacol ester intermediate. The intermediate boronate ester was then treated with peroxide in tetrahydrofuran with methanol and adhered to silica gel. The desired compound 9 with residual boronate pinacol ester was isolated by flash silica gel chromatography (90 g, 2:1 hexanes:ethyl acetate). The compound mixture was dissolved in peroxide in tetrahydrofuran, adhered to silica gel, and purified by flash silica gel chromatography (55 g, step gradient in dichloromethane: 0, 2, 5, and 10% ethyl acetate) to yield 71 mg (10%) of 9 as an off-white solid. ESI-MS m/z 352.1 $[M+H]^+$. Analysis: Calcd for $C_{20}H_{18}FN_3O_2$½$H_2O$: C, 66.66; H, 5.31; N, 11.66. Found: C, 66.83; H, 5.16; N, 11.43. $^1H$ NMR (500 MHz, DMSO-$d_6$) δ 10.04 (s, 1H), 9.92 (s, 1H), 8.73 (d, J=2.1 Hz, 1H), 8.06 (dd, J=9.2 Hz, 2.2 Hz, 1H), 7.80-7.75 (m, 2H), 7.18 (t, J=8.8 Hz, 2H), 7.09 (t, J=7.8 Hz, 1H), 6.98 (d, J=7.4 Hz, 1H), 6.86 (d, J=8.1 Hz, 1H), 6.75-6.72 (m, 2H), 4.76 (s, 2H), 3.17 (s, 3H). $IC_{50}$ in whole cell assay (Pharmacology Example 1)=0.59±0.09 μM.

SYNTHESIS EXAMPLE 8

Preparation of Compound 10

Compound 7 (522 mg, 1.17 mmol) was suspended with stirring in methanol (10 mL), and 4.5 M $KHF_2$ (1.1 mL, 5.89 mmol) was added dropwise by pipette. After stirring for an hour, the reaction was diluted with methanol and dried under vacuum to yield an oily solid, which was diluted with water. Sonication yielded a precipitate, which was isolated by vacuum filtration and dried in a vacuum desiccator. The solid was dissolved in acetonitrile (10 mL), and stirred with trimethylsilylchloride (0.44 mL, 3.5 mmol) and water (63 μL, 3.5 mmol) at room temperature. After stirring for an hour, the reaction was quenched with saturated sodium bicarbonate (2 mL). After several minutes of stirring, the reaction was diluted with water to a volume of 80 mL, and the precipitate that formed was isolated by vacuum filtration to yield 10 as white solid (323 mg, 76%). ESI-MS m/z 366.2 $[M+H]^+$. $^1H$ NMR (500 MHz, DMSO-$d_6$) δ 10.05 (s, 1H), 8.26 (dd, J=9.0 Hz, 2.0 Hz, 1H), 7.63-7.60 (m, 2H), 7.54 (d, J=1.9 Hz, 1H), 7.45-7.36 (m, 3H), 7.29 (t, J=7.1 Hz, 1H), 7.14 (t, J=8.8 Hz, 2H), 7.00 (d, J=9.2 Hz, 1H), 4.83-4.75 (m, 2H). $IC_{50}$ in whole cell assay (Pharmacology Example 1)=1.7±0.2 μM.

SYNTHESIS EXAMPLE 9

Preparation of Compound 12

2-Chloropyrimidine-5-carboxylic acid (1.99 g, 12.5 mmol) was dissolved in anhydrous DMF (10 mL) under an $N_2$ atmosphere. 4-Fluoroaniline (1.2 mL, 12.5 mmol) and EEDQ (3.11 g, 12.6 mmol) were added and stirred at room temperature for 40 hours. The product was partitioned between deionized water and ethyl acetate. The aqueous layer was washed with ethyl acetate, and the combined ethyl acetate layers were dried over sodium sulfate, filtered, and dried in vacu. The crude product was dissolved in ethyl acetate and minimal methanol and adhered to silica gel (28 g) The silica adhered compound was purified by flash silica gel chromotography (340 g, 3:1 hexanes/ethyl acetate) to yield 1.2 g (37%) of 12 as a white solid. ESI-MS m/z 252.1 $[M+H]^+$. $^1H$ NMR (500 MHz, DMSO-$d_6$) δ 10.67 (s, 1H), 9.23 (s, 2H), 7.78-7.75 (m, 2H), 7.25 (t, J=8.8 Hz, 2H).

SYNTHESIS EXAMPLE 10

Preparation of Compound 14

Compound 2 (1.486 g, 5.04 mmol), 4-bromo-N-methylbenzylamine (1.00 mL, 5.00 mmol) and triethylamine (1.40 mL, 10.0 mmol) were dissolved in anhydrous dimethylformamide (10 mL) and placed in a pressure bottle, under an $N_2$ atmosphere. The reaction was heated to 130° C. for 3 days. The reaction was cooled to room temperature and diluted into deionized water (250 mL), yielding a fluffy white precipitate with a few brown clumps. After cooling briefly and sonicating and crushing the clumps, the precipitate was collected by vacuum filtration, washing with deionized water, and dried under vacuum. The crude product was dissolved in ethyl acetate and adhered to silica gel (20 g). The silica adhered compound was purified by flash silica gel chromatography (200 g silica, 3:2 hexanes:ethyl acetate) to yield 1.67 g (81%) of 14 as a white solid. ESI-MS m/z 414.1/416.1 $[M+H]^+$. Analysis: Calcd for $C_{20}H_{17}BrFN_3O$: C, 57.98; H, 4.14; N, 10.14. Found: C, 57.82; H, 4.20; N, 10.01. $^1H$ NMR (500 MHz, DMSO-$d_6$) δ 10.04 (s, 1H), 8.72 (s, 1H), 8.07 (d, J=9.3 Hz, 1H), 7.77-7.75 (m, 2H), 7.53 (d, J=7.0 Hz, 2H), 7.20-7.16 (m, 4H), 6.76 (d, J=9.7 Hz, 1H), 4.86 (s, 2H), 3.11 (s, 3H).

SYNTHESIS EXAMPLE 11

Preparation of Compound 15

Compound 12 (254 mg, 1.01 mmol), 4-bromo-N-methylbenzylamine (200 μL, 1.00 mmol) and triethylamine (280 μL, 2.01 mmol) were dissolved in anhydrous dimethylformamide (2 mL) and placed in a pressure bottle, under an $N_2$ atmosphere. The reaction was stirred at room temperature for 3 hours, then diluted dropwise into deionized water (60 mL), yielding a fluffy white precipitate. After cooling briefly, the precipitate was collected by vacuum filtration, washing with deionized water, and dried under vacuum to yield 410 mg (99%) of 15 as a white solid. ESI-MS m/z 415.1/417.1 $[M+H]^+$. $^1H$ NMR (500 MHz, DMSO-$d_6$) δ 10.16 (s, 1H), 8.90 (s, 1H), 7.75-7.73 (m, 2H), 7.54 (d, J=8.6 Hz, 2H), 7.23-7.17 (m, 4H), 4.92 (s, 2H), 3.18 (s, 3H).

SYNTHESIS EXAMPLE 12

Preparation of Compound 16

Compound 14 (1.65 g, 4.0 mmol) was dissolved in anhydrous dimethylformamide (10 mL) and degassed under vacuum. A pressure bottle was charged with $PdCl_2$ (dppf) (244 mg, 0.299 mmol), bis(pinacolato) diboron (3.05 g, 12.0 mmol) and potassium acetate (1.17 g, 11.9 mmol), along with a stir bar. The DMF solution was added to the pressure bottle with an oven-dried pipette, rinsing with dry DMF (2×5 mL). The tube was sealed under nitrogen gas and heated at 80° C. for 8.5 hours, then cooled to room temperature. The reaction was filtered through Celite, rinsing with DMF, dried in vacu, and partitioned between water and ethyl acetate, and the aqueous layer was washed with ethyl acetate. The combined ethyl acetate layers were dried over $Na_2SO_4$, and filtered through a pad of silica gel (ethyl acetate). The filtrate was dried under vacuum, dissolved in ethyl acetate, and adhered to silica gel (20 g). The silica adhered compound was purified by flash silica gel chromatography (200 g, 2:1 hexanes:ethyl acetate) to yield 1.67 g (91%) of 16 as a white flaky solid. ESI-MS m/z 462.3 $[M+H]^+$. $^1H$ NMR (500 MHz, DMSO-$d_6$) δ 10.03 (s, 1H), 8.73 (d, J=2.0 Hz, 1H), 8.06 (dd, J=9.2 Hz, 2.5 Hz, 1H), 7.77-7.74 (m, 2H), 7.65 (d, J=7.2 Hz, 2H), 7.24 (d, J=7.2 Hz, 2H), 7.17 (t, J=8.9 Hz, 2H), 6.75 (d, J=8.8 Hz, 1H), 4.91 (s, 2H), 3.11 (s, 3H), 1.28 (s, 12H).

SYNTHESIS EXAMPLE 13

Preparation of Compound 17

Compound 15 (395 mg, 0.951 mmol) was dissolved in anhydrous dimethylformamide (4 mL) and degassed under vacuum. A pressure bottle was charged with $PdCl_2$(dppf) (60 mg, 0.074 mmol), bis(pinacolato) diboron (726 mg, 2.86 mmol) and potassium acetate (280 mg, 2.85 mmol), along with a stir bar. The DMF solution was added to the pressure bottle with an oven-dried pipette, rinsing with dry DMF (2×2 mL). The tube was sealed under nitrogen gas and heated at 80° C. for 6.5 hours, then cooled to room temperature. The reaction was filtered through Celite, rinsing with DMF, dried in vacu, and partitioned between water and ethyl acetate, and the aqueous layer was washed with ethyl acetate. The combined ethyl acetate layers were dried over $Na_2SO_4$, and filtered through a pad of silica gel (ethyl acetate). The filtrate was dried under vacuum, dissolved in ethyl acetate, and adhered to silica gel (7.5 g). The silica adhered compound was purified by flash silica gel chromatography (78 g, 5:2 hexanes:ethyl acetate) to yield 379 mg (86%) of 17 as a white solid. ESI-MS m/z 463.2 $[M+H]^+$. $^1H$ NMR (500 MHz, DMSO-$d_6$) δ 10.15 (s, 1H), 8.90 (s, 2H), 7.75-7.72 (m, 2H), 7.66 (d, J=7.6 Hz, 2H), 7.26 (d, J=7.6 Hz, 2H), 7.19 (t, J=8.9 Hz, 2H), 4.98 (s, 2H), 3.17 (s, 3H), 1.28 (s, 12H).

SYNTHESIS EXAMPLE 14

Preparation of Compound 18

Compound 16 (1.64 g, 3.55 mmol) was suspended with stirring in methanol (50 mL), and 4.5 M $KHF_2$ (4.0 mL, 18.0 mmol) was in portions by pipette. After stirring for 1.5 hours, the reaction was diluted with methanol and dried under vacuum to yield a white solid, which was diluted with water. Sonication yielded a precipitate, which was isolated by vacuum filtration and dried in a vacuum desiccator. The solid (1.43 g, 3.25 mmol) was dissolved in acetonitrile (36 mL), and stirred with trimethylsilylchloride (1.24 mL, 9.77 mmol) and water (176 μL, 9.78 mmol) at room temperature. After stirring for 1.5 hours, the reaction was quenched with saturated sodium bicarbonate (6 mL). After several minutes of stirring, the reaction was diluted with water to dissolve the compound and dried in vacu. The residual solid was suspended in water with sonication, and the precipitate that formed was isolated by vacuum filtration and dried in a vacuum desiccator to yield 18 as white solid (1.33 g, 99%). ESI-MS m/z 380.2 $[M+H]^+$. $^1H$ NMR (500 MHz, DMSO-$d_6$) δ 10.10 (s, 1H), 8.72 (s, 1H), 8.11 (d, J=8.6 Hz, 1H), 7.76-7.75 (m, 4H), 7.20-7.16 (m, 4H), 6.84 (d, J=8.5 Hz, 1H), 4.90 (s, 2H), 3.15 (s, 3H). $IC_{50}$ in whole cell assay (Pharmacology Example 1)=0.247±0.035 μM.

SYNTHESIS EXAMPLE 15

Preparation of Compound 19

Compound 17 (365 mg, 0.789 mmol) was suspended with stirring in methanol (7 mL), and 4.5 M $KHF_2$ (0.88 mL, 3.96 mmol) was in portions by pipette. After stirring for 1.5 hours, the reaction was diluted with methanol and dried under vacuum to yield a white solid, which was diluted with water. Sonication yielded a precipitate, which was isolated by vacuum filtration and dried in a vacuum desiccator. The solid (322 mg, 0.728 mmol) was dissolved in acetonitrile (6 mL), and stirred with trimethylsilylchloride (276 μL, 2.18 mmol) and water (40 μL, 2.22 mmol) at room temperature. After stirring for 1.5 hours, the reaction was quenched with saturated sodium bicarbonate (1.3 mL). After several minutes of stirring, the reaction was concentrated in vacu and suspended in water (40 mL) with sonication, yielding a fluffy white solid, which was isolated by vacuum filtration and dried in a vacuum desiccator to yield 19 as white solid (280 mg, 93%). ESI-MS m/z 381.2 $[M+H]^+$. $^1H$ NMR (500 MHz, DMSO-$d_6$) δ 10.16 (s, 1H), 8.91 (s, 2H), 7.76-7.73 (m, 4H), 7.21-7.17 (m, 4H), 4.96 (s, 2H), 3.18 (s, 3H). $IC_{50}$ in whole cell assay (Pharmacology Example 1)=0.244±0.015 μM.

PHARMACOLOGY EXAMPLE 1

In Vitro Inhibition of Intracellular Calcium Release by Compound 9

An in vitro assay showed inhibition of CXCR2-mediated intracellular calcium release by treatment with compound 9 ($IC_{50}$ =586±91 nM). Briefly, human neutrophils were suspended in $HBSS^-$ (without $Ca^{2+}$ and $Mg^{2+}$) containing 10 mM HEPES and FLIPR Calcium 3 dye ($3.1\times10^7$ cells in total volume 1.7 mL). Cells were aliquoted (200 μL of the cell suspension per tube, 8 tubes total) and 2 μL of compound 9 (with appropriate dilutions) were added to each of 6 tubes. The tested concentrations of compound 9 were 156 nM, 312 nM, 625 nM, 1250 nM, 2500 nM and 5000 nM. As controls, 2 μL of DMSO (1% final concentration) were added to 2 other tubes. Cells were incubated for 30 min at 37° C. After dye loading, tubes were centrifuged at 6,000 rpm for 1 min, supernatant was removed and the cell pellet was re-suspended in 200 μL of $HBSS^+$ (with $Ca^{2+}$ and $Mg^{2+}$) containing 10 mM HEPES. The test compound or DMSO (control) was added again at the same concentrations that were used during cell loading. The cell suspension was aliquoted into a 96-well Reading Plate (Corning) in a volume of 90 μL ($10^5$ cells/well). The Compound Plate contained agonist (GROα in $HBSS^-$) or $HBSS^-$ (control). After 15 sec of reading the basal level of fluorescence by FlexStation II, 10 μL of GROα or $HBSS^-$ were automatically transferred from the Compound Plate into the Reading Plate (final concentration of GROα was 25 nM). Changes in fluorescence were monitored ($\lambda_{ex}$=485 nm, $\lambda_{em}$=525 nm) every 5 s for 240 to 500 s at room temperature.

The maximum change in fluorescence, expressed in arbitrary units over baseline (Max-Min), was used to determine the GROα response. The effect of each compound on the GROα response was normalized and expressed as a percent of the DMSO control, which was designated as "100% response." Curve fitting and calculation of the compound inhibitory concentration that reduces the level of the GROα response by 50% ($IC_{50}$), or the compound agonist concentration that increases the level of the calcium release by 50% of the maximum agonist-induced change ($EC_{50}$) were determined by nonlinear regression analysis of the dose-response curves generated using Prism 4 (GraphPad Software, Inc., San Diego, Calif.).

TABLE 1

| Inhibition of CXCR2 | | | | |
|---|---|---|---|---|
| Compound Name | Compound Number | Molecular Weight | Structure | $IC_{50}$ (μM) |
| SX-626 | 9 | 351.37 | 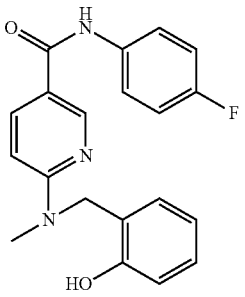 | 0.586 ± 0.91 |
| SX-627 | 7 | 447.31 | 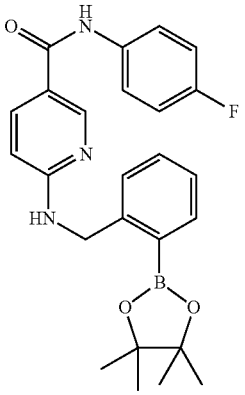 | 1.5 ± 0.3 |
| SX-628 | 8 | 379.19 | 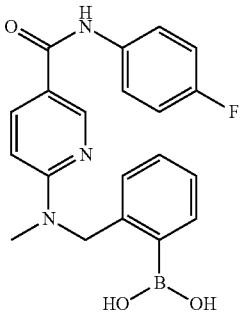 | 1.0 ± 0.2 |
| SX-629 | 10 | 365.17 | 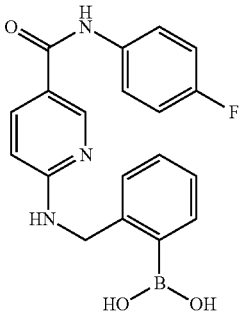 | 1.7 ± 0.2 |

TABLE 1-continued

| Inhibition of CXCR2 | | | | |
|---|---|---|---|---|
| Compound Name | Compound Number | Molecular Weight | Structure | $IC_{50}$ (μM) |
| SX-632 | 18 | 379.19 | 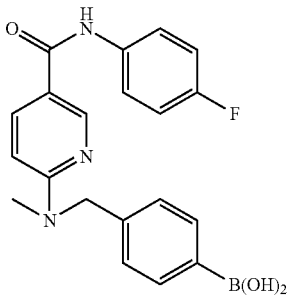 | 0.247 ± 0.35 |
| SX-633 | 19 | 380.18 | 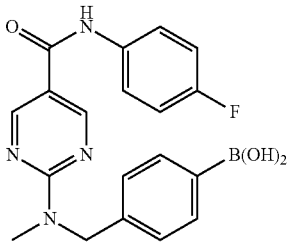 | 0.244 ± 0.15 |

We claim:

1. A compound comprising a compound from formula ([2] *1*):

[(2)] *(1)*

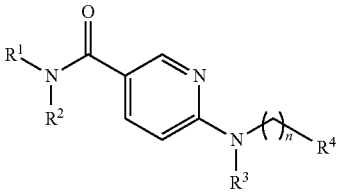

wherein $R^1$ is selected from the group consisting of hydrogen, 2- or 3- or 4-halo-phenyl, heteroalkyl, n-propyl, isopropyl, n-butyl, t-butyl, n-pentyl, heptyl, nonyl, decyl, unsaturated alkyl, alkyl substituted with 1-4 substituents, aryl, arylalkyl, heteroaryl, heteroarylalkyl, cycloalkyl, cycloalkylalkyl, heterocyclyl, and [heterocyclylalkyl] *heterocycloalkylalkyl*;

wherein $R^2$ is selected from the group consisting of 2- or 3- or 4-halo-phenyl, [heteroalkyl,] ethyl, [n-propyl,] isopropyl, n-butyl, t-butyl, n-pentyl, heptyl, nonyl, decyl, unsaturated alkyl, alkyl substituted with 1-4 substituents *selected from the group consisting of hydroxy, alkylamino, boronyl, carboxy, nitro, and cyano*, aryl, arylalkyl, heteroaryl, heteroarylalkyl, cycloalkyl, cycloalkylalkyl *comprising a monocyclic or multicyclic ring system comprising 3 to 5 or 7 to 10 carbon atoms*, heterocyclyl, and [heterocyclylalkyl] *heterocycloalkylalkyl*, wherein aryl [is] *and heteroaryl are independently unsubstituted or* substituted with one or more substituents selected from the group consisting of —C(O)R, —OR, [alkyl,] aryl, —N(H)R, —N(R)R, —S—R, —$N_3$, —B(R)R, —$B(OH)_2$, —$B(OR)_2$, —C(O)OH, —C(O)OR, —$C(O)NH_2$, —$S(O)_2NH_2$, —C(O)N(H)R, —C(O)N(R)R, —SH, —S—R, —$NO_2$, cyano, halo, haloalkyl, haloalkoxy, heterocyclyl, heteroalkyl, —OH, —OC(O)R, —C(O)R and —C(O)$CH_aX_b$, wherein a+b=3 and X is selected from the group consisting of F, Cl or Br, and wherein R is alkyl having less than twelve carbons;

wherein $R^3$ is selected from the group consisting of hydrogen, heteroalkyl, methyl, n-propyl, isopropyl, n-butyl, t-butyl, n-pentyl, heptyl, nonyl, decyl, unsaturated alkyl, alkyl substituted with 1-4 substituents, aminoalkyl, aryl, arylalkyl, carboxyalkyl, heteroaryl, heteroarylalkyl, *wherein the heteroaryl of the heteroarylalkyl is selected from pyridyl, pyrazinyl, furanyl, thienyl, pyrimidinyl, isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, and benzothiazolyl,* cycloalkyl, cycloalkylalkyl, heterocyclyl, [heterocyclylalkyl] *heterocycloalkylalkyl*, —$B(R^5R^6)$, —$BF_3^-M^+$, —$R^7$—$B(R^5R^6)$, —$R^7$—$BF_3^-M^+$, [$R^7$,] —C(O)—$R^7$, —O—$R^7$, —$S(O)_y$—$R^7$ (wherein y=0, 1, or 2), —P(O)—($R^5R^6$), —$N(R^8R^9)$, carboxylates, amines, phosphonates, and phosphates;

wherein $R^4$ is selected from the group consisting of [heteroalkyl, methyl, n-propyl,] isopropyl, n-butyl, [t-butyl,] n-pentyl, heptyl, nonyl, decyl, unsaturated alkyl, [alkyl substituted with 1-4 substituents,] aminoalkyl, carboxyalkyl, [heteroaryl,] heteroarylalkyl, *substituted* cycloalkyl, *unsubstituted cycloalkyl of 5 to 7 ring carbons,* cycloalkylalkyl, heterocyclyl, [heterocyclylalkyl] *heterocycloalkylalkyl, wherein the heterocyclic ring of the heterocycloalkylalkyl is selected from piperidyl, morpholinyl, thiomorpholinyl, thiazolidinyl, 1,3-dioxolanyl, 1,4-dioxolanyl, tetrahydrofuranyl, tetrahydrothiophenyl, and tetrahydrothiopyranyl,* —$B(R^5R^6)$, —$BF_3^-M^+$, —$R^7$—$B(R^5R^6)$, —$R^7$—$BF_3^-M^+$, [—C(O)—$R^7$] —$C(O)R^{10}$, —O—$R^7$, —$S(O)_y$—$R^7$ (wherein y=0, 1, or 2), —P(O)—($R^5R^6$), —$N(R^8R^9)$, [carboxylates, amines,] phosphonates, [and] phosphates, *aryl substituted with one or more substituents selected from the group consisting of —C(O)R, —$OCF_3$, —O-ethyl, —O-propyl, —O-butyl, —O-pentyl, —O-hexyl, —O-heptyl, —O-octyl, —O-nonyl, —O-decyl, —O-undecyl, —O-dodecyl, —CF, ethyl, propyl, butyl, pentyl, hexyl, heptyl, octyl, nonyl, decyl, undecyl, dodecyl, aryl, —N(H)R, —N(R)R, —S—R, —$NH_2$, —$N_3$, —B(R)R, —$B(OH)_2$, —$B(OR)_2$, —C(O)OH, —C(O)OR, —$C(O)NH_2$, —$S(O)_2NH_2$, —C(O)N(H)R, —C(O)N(R)R, —SH, —S—R, —$NO_2$, cyano, halo, haloalkyl, haloalkoxy, heterocyclyl, heteroalkyl, —OH, —OC(O)R, —C(O)R and —C(O)$CH_aX_b$, wherein a+b=3 and X is selected from the group consisting of F, Cl or Br, and wherein R is alkyl having less than twelve carbons, and heteroaryl, wherein the heteroaryl is selected from the group consisting of pyridyl, pyrazinyl, furanyl, thienyl, pyrimidinyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, imidazo(1,2-a)pyridinyl, imidazo(2,1-b)thiazolyl, benzofurazanyl, indolyl, azaindolyl, benzimidazolyl, benzothienyl, quinolinyl, imidazolyl, thienopyridyl,*

*quinazolinyl, thienopyrimidyl, pyrrolopyridyl, imidazopyridyl, isoquinolinyl, benzoazaindolyl, 1,2,4-triazinyl, and benzothiazolyl, and wherein the heteroaryl is unsubstituted or substituted by one or more substituents selected from acyl, alkoxy, aryl, aminoalkyl, alkylthio, amino, azido, boronyl, carboxy, alkoxycarbonyl, aminocarbonyl, aminosulfonyl, alkylaminocarbonyl, cyano, halo, haloalkyl, haloalkoxy, heterocyclyl, heteroalkyl, hydroxyl, acyloxy, ketone, substituted halomethylketone, mercapto, and nitro*;

wherein $R^7$ is selected from the group consisting of alkyl, aryl, arylalkyl, cycloalkyl, heteroaryl, [heteroarylalkyl ,] *heteroarylalkyl,* heterocyclyl and [heterocyclylalkyl] *heterocycloalkylalkyl*;

wherein $M^+$ is a Group I or a Group II metal;

wherein $R^5$ and $R^6$ are independently hydrogen, hydroxyl, aryloxy, or alkoxy, or wherein $R^5$ and $R^6$ together form a cyclic ester, or an acid anhydride (either mixed or symmetrical);

wherein $R^8$ [and $R^9$ are independently] *is* selected from hydrogen, alkyl, haloalkyl, aryl, cycloalkyl, arylalkyl, heteroalkyl, [hetercyclyl] *heterocyclyl* and [heterocyclylalkyl] *heterocycloalkylalkyl*; *and wherein $R^9$ is selected from haloalkyl, aryl, cycloalkyl, arylalkyl, heteroalkyl, heterocyclyl and heterocycloalkylalkyl;* $R^8$ and $R^9$ are both oxygen to form a nitro group; or $R^8$ and $R^9$ together with the nitrogen to which they are attached form a heterocyclyl; [and]

*wherein $R^{10}$ is selected from the group consisting of aryl, arylalkyl, cycloalkyl, heteroaryl, heteroarylalkyl, heterocyclyl and heterocycloalkylalkyl; and* wherein n is 1; [and] *or*

*a pharmaceutically acceptable solvated or unsolvated form thereof; a pharmaceutically acceptable salt thereof; or a* pharmaceutical [compositions] *composition* thereof.

2. The compound of claim 1 wherein $R^2$ is 4-fluorophenyl.

3. The compound of claim 1 wherein $R^4$ is 4-phenylboronic acid.

[4. A pharmaceutical composition comprising a compound of formula (2):

(2)

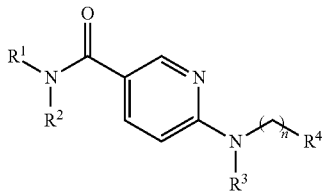

wherein $R^1$ is selected from the group consisting of hydrogen, 2- or 3- or 4-halo-phenyl, heteroalkyl, n-propyl, isopropyl, n-butyl, t-butyl, n-pentyl, heptyl, nonyl, decyl, unsaturated alkyl, alkyl substituted with 1-4 substituents, aryl, arylalkyl, heteroaryl, heteroarylalkyl, cycloalkyl, cycloalkylalkyl, heterocyclyl, and heterocyclylalkyl;

wherein $R^2$ is selected from the group consisting of 2- or 3- or 4-halo-phenyl, heteroalkyl, ethyl, n-propyl, isopropyl, n-butyl, t-butyl, n-pentyl, heptyl, nonyl, decyl, unsaturated alkyl, alkyl substituted with 1-4 substituents, aryl, arylalkyl, heteroaryl, heteroarylalkyl, cycloalkyl, cycloalkylalkyl, heterocyclyl, and heterocyclylalkyl, wherein aryl is substituted with one or more substituents selected from the group consisting of —C(O)R, —OR, alkyl, aryl, —N(H)R, —N(R)R, —S—R, —$N_3$, —B(R)R, —$B(OH)_2$, —$B(OR)_2$, —C(O)OH, —C(O)OR, —$C(O)NH_2$, —$S(O)_2NH_2$, —C(O)N(H)R, —C(O)N(R)R, —SH, —S—R, —$NO_2$, cyano, halo, haloalkyl, haloalkoxy, heterocyclyl, heteroalkyl, —OH, —OC(O)R, —C(O)R and —C(O)$CH_{aXb}$, wherein a+b=3 and X is selected from the group consisting of F, Cl or Br, and wherein R is alkyl having less than twelve carbons;

wherein $R^3$ is selected from the group consisting of hydrogen, heteroalkyl, methyl, n-propyl, isopropyl, n-butyl, t-butyl, n-pentyl, heptyl, nonyl, decyl, unsaturated alkyl, alkyl substituted with 1-4 substituents, aminoalkyl, aryl, arylalkyl, carboxyalkyl, heteroaryl, heteroarylalkyl, cycloalkyl, cycloalkylalkyl, heterocyclyl, heterocyclylalkyl, —$B(R^5R^6)$, —$BF_3^-M^+$, —$R^7$—$B(R^5R^6)$, —$R^7$—$BF_3^-M^+$, $R^7$,—C(O)—$R^7$, —O—$R^7$, —$S(O)_y$—$R^7$ (wherein y=0, 1, or 2), —P(O)—$(R^5R^6)$, —$N(R^8R^9)$, carboxylates, amines, phosphonates, and phosphates;

wherein $R^4$ is selected from the group consisting of heteroalkyl, methyl, n-propyl, isopropyl, n-butyl, t-butyl, n-pentyl, heptyl, nonyl, decyl, unsaturated alkyl, alkyl substituted with 1-4 substituents, aminoalkyl, aryl, arylalkyl, carboxyalkyl, heteroaryl, heteroarylalkyl, cycloalkyl, cycloalkylalkyl, heterocyclyl, heterocyclylalkyl, —$B(R^5R^6)$, —$BF_3^-M^+$, —$R^7$—$B(R^5R^6)$, —$R^7$—$BF_3^-M^+$, —(CO)—$R^7$, —O—$R^7$, —$S(O)_y$—$R^7$ (wherein y=0, 1, or 2), —P(O)—$(R^5R^6)$, —$N(R^8R^9)$, carboxylates, amines, phosphonates, and phosphates;

wherein $R^7$ is selected from the group consisting of alkyl, aryl, arylalkyl, cycloalkyl, heteroaryl, heteroarylalkyl , heterocyclyl and heterocyclylalkyl;

wherein $M^+$ is a Group I or a Group II metal;

wherein $R^5$ and $R^6$ are independently selected from the group consisting of hydrogen, hydroxyl, aryloxy, or alkoxy, or wherein $R^5$ and $R^6$ together form a cyclic ester, or an acid anhydride;

wherein $R^8$ and $R^9$ are independently selected from the group consisting of hydrogen, alkyl, haloalkyl, aryl, cycloalkyl, arylalkyl, heteroalkyl, hetercyclyl and heterocyclylalkyl; $R^8$ and $R^9$ are both oxygen to form a nitro group; or $R^8$ and $R^9$ together with the nitrogen to which they are attached , form a heterocyclyl; and wherein $X^1$ is carbon;

wherein n is 1, and pharmaceutical compositions thereof.]

[5. The pharmaceutical composition of claim 4, wherein $R^2$ is 4-fluoro-phenyl.]

[6. The pharmaceutical composition of claim 4, wherein $R^4$ is 4-phenylboronic acid.]

*7. The compound of claim 1, wherein $R^1$ is hydrogen.*

*8. The compound of claim 1, wherein $R^3$ is hydrogen.*

*9. The compound of claim 1, wherein $R^3$ is methyl.*

*10. The compound of claim 1, wherein $R^4$ is —$B(R^5R^6)$, —$BF_3^-M^+$, —$R^7$—$B(R^5R^6)$, or —$R^7$—$BF_3^-M^+$.*

*11. The compound of claim 10, wherein $R^7$ is aryl.*

*12. The compound of claim 1, wherein $R^4$ is an heteroaryl, wherein the heteroaryl is substituted with a halide, —OH, or —$B(R^5R^6)$.*

*13. The compound of claim 12, wherein heteroaryl is substituted with —$B(R^5R^6)$.*

*14. The compound of claim 13, wherein heteroaryl is pyridine and —$B(R^5R^6)$ is —$R^7$—$B(OH)_2$.*

15. The compound of claim 13, wherein heteroaryl is pyridine and —B($R^5R^6$) is

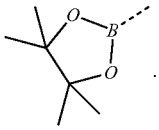

16. A compound comprising a compound from formula (1):

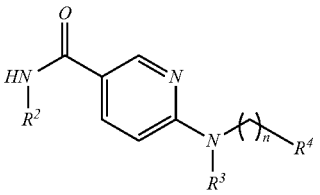

(1)

wherein $R^2$ is 2-, 3-, or 4-halophenyl;

wherein $R^3$ is hydrogen, heteroalkyl, alkyl, aminoalkyl, aryl, arylalkyl, carboxyalkyl, heteroaryl, heteroarylalkyl, cycloalkyl, cycloalkylalkyl, heterocyclyl, heterocycloalkylalkyl, carboxylate, amine, phosphonate, phosphate, —B($R^5R^6$), —$BF_3^-M^+$, —$R^7$—B($R^5R^6$), —$R^7$—$BF_3^-M^+$, —C(O)—$R^7$, —O—$R^7$, —S(O)$_y$—$R^7$ (wherein y=0, 1, or 2), —P(O)—($R^5R^6$), or —N($R^8R^9$), wherein $R^4$ is heteroalkyl, n-propyl, isopropyl, n-butyl, t-butyl, n-pentyl, heptyl, nonyl, decyl, unsaturated alkyl, alkyl substituted with 1-4 substituents, aminoalkyl, naphthyl, indenyl, tetrahydronaphthyl, indanyl, anthracenyl, fluorenyl, substituted aryl, arylalkyl, carboxyalkyl, heteroaryl, heteroarylalkyl, substituted cycloalkyl, unsubstituted cycloalkyl of 5 to 7 ring carbons, cycloalkylalkyl, heterocyclyl, heterocycloalkylalkyl, carboxylate, amine, phosphonate, phosphate, —B($R^5R^6$), —$BF_3^-M^+$, —$R^7$—B($R^5R^6$), —$R^7BF_3^-M^+$, —C(O)—$R^7$, —O—$R^7$, —S(O)$_y$—$R^7$ (wherein y=0, 1, or 2), —P(O)—($R^5R^6$), or —N($R^8R^9$); wherein $M^+$ is a Group I or a Group II metal;

wherein $R^5$ and $R^6$ are independently hydrogen, hydroxyl, aryloxy, or alkoxy, or wherein $R^5$ and $R^6$ together form a cyclic ester, or an acid anhydride (either mixed or symmetrical);

wherein $R^7$ is alkyl, aryl, arylalkyl, cycloalkyl, heteroaryl, heteroarylalkyl, heterocyclyl or heterocycloalkylalkyl;

wherein $R^8$ and $R^9$ are independently hydrogen, alkyl, haloalkyl, aryl, cycloalkyl, arylalkyl, heteroalkyl, heterocyclyl or heterocycloalkylalkyl; $R^8$ and $R^9$ are both oxygen to form a nitro group; or $R^8$ and $R^9$ together with the nitrogen to which they are attached form a heterocyclyl; and wherein n is 1;

a pharmaceutically acceptable solvated or unsolvated form thereof; a pharmaceutically acceptable salt thereof; or a pharmaceutical composition thereof.

17. A compound comprising a compound from formula (1):

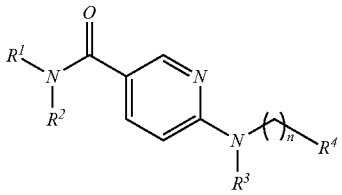

(1)

wherein $R^1$ is hydrogen, 2- or 3- or 4-halo-phenyl, heteroalkyl, methyl, ethyl, isopropyl, butyl, pentyl, hexyl, heptyl, octyl, nonyl, decyl, undecyl, dodecyl, aryl, arylalkyl, heteroaryl, heteroarylalkyl, cycloalkyl, cycloalkylalkyl, heterocyclyl, or heterocycloalkylalkyl;

wherein $R^2$ is 2- or 3- or 4-halo-phenyl, methyl, ethyl, isopropyl, butyl, pentyl, hexyl, heptyl, octyl, nonyl, decyl, undecyl, dodecyl, aryl, arylalkyl, heteroaryl, heteroarylalkyl, cycloalkyl, cycloalkylalkyl, heterocyclyl, or heterocycloalkylalkyl;

wherein $R^3$ is hydrogen, heteroalkyl, alkyl, aminoalkyl, aryl, arylalkyl, carboxyalkyl, heteroaryl, heteroarylalkyl, wherein the heteroaryl of the heteroarylalkyl is selected from pyridyl, pyrazinyl, furanyl, thienyl, pyrimidinyl, isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, and benzothiazolyl, cycloalkyl, cycloalkylalkyl, heterocyclyl, heterocycloalkylalkyl, carboxylate, amine, phosphonate, or phosphate;

wherein $R^4$ is —B($R^5R^6$), —$BF_3^-M^+$, —$R^7$—B($R^5R^6$), —$R^7$—$BF_3^-M^+$, —C(O)—$R^7$, —O—$R^7$, —S(O)$_y$—$R^7$ (wherein y=0, 1, or 2), —P(O)—($R^5R^6$), —N($R^8R^9$), cycloalkyl, piperidyl, pyrrolidinyl, piperazinyl, morpholinyl, thiomorpholinyl, thiazolidinyl, 1,3-dioxolanyl, 1,4-dioxanyl, tetrahydrofuranyl, tetrahydrothiophenyl, tetrahydrothiopyranyl, heterocycloalkylalkyl, wherein the heterocyclic ring of the heterocycloalkylalkyl is selected from piperidyl, pyrrolidinyl, morpholinyl, thiomorpholinyl, thiazolidinyl, 1,3-dioxolanyl, 1,4-dioxanyl, tetrahydrofuranyl, tetrahydropyranyl, tetrahydrothiophenyl, or tetrahydrothiopyranyl, or an aryl substituted with a chloride, bromide, iodide, —OH, —OC(O)R, —$OCF_3$, —C(O)R, —$CF_3$, ethyl, propyl, butyl, pentyl, hexyl, heptyl, octyl, nonyl, decyl, undecyl, dodecyl, —$NO_2$, or —B($R^5R^6$), wherein R is methyl, ethyl, n-propyl, butyl, pentyl, hexyl, heptyl, octyl, nonyl, decyl, undecyl, or dodecyl, and $M^+$ is a Group I or a Group II metal;

wherein $R^5$ and $R^6$ are independently hydrogen, hydroxyl, aryloxy, or alkoxy, or wherein $R^5$ and $R^6$ together form a cyclic ester, or an acid anhydride (either mixed or symmetrical);

wherein $R^7$ is alkyl, aryl, arylalkyl, cycloalkyl, heteroaryl, heteroarylalkyl, heterocyclyl or heterocycloalkylalkyl;

wherein $R^8$ and $R^9$ are independently hydrogen, alkyl, haloalkyl, aryl, cycloalkyl, arylalkyl, heteroalkyl, heterocyclyl or heterocycloalkylalkyl; $R^8$ and $R^9$ are both

*oxygen to form a nitro group; or $R^8$ and $R^9$ together with the nitrogen to which they are attached form a heterocyclyl; and*

*wherein n is 1; or*

*a pharmaceutically acceptable solvated or unsolvated form thereof; a pharmaceutically acceptable salt thereof; or a pharmaceutical composition thereof.*

*18. The compound of claim 17, wherein the compound is of formula SX-626, SX-627, SX-628, SX-629, or SX-632, a pharmaceutically acceptable solvated or unsolvated form thereof; a pharmaceutically acceptable salt thereof; or a pharmaceutical composition thereof*

*SX-626*

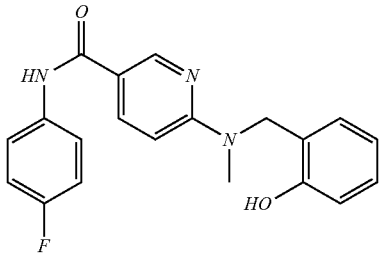

*SX-627*

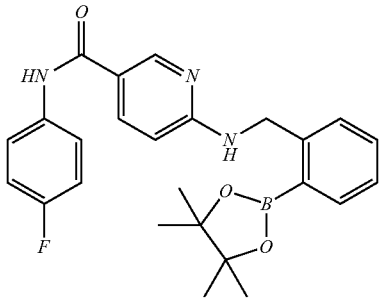

*SX-628*

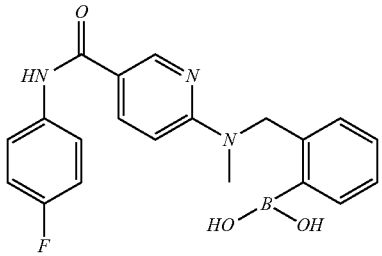

*-continued*

*SX-629*

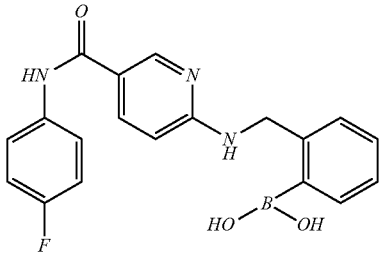

*SX-632*

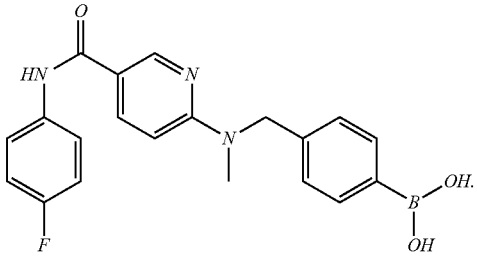

*19. The compound of claim 17, wherein $R^1$ is hydrogen.*

*20. The compound of claim 17, wherein $R^3$ is hydrogen.*

*21. The compound of claim 17, wherein $R^3$ is methyl.*

*22. The compound of claim 17, wherein $R^4$ is an aryl substituted with a chloride, bromide, iodide, —OH, —OC(O)R, —$OCF_3$, —C(O)R, —$CF_3$, ethyl, propyl, butyl, pentyl, hexyl, heptyl, octyl, nonyl, decyl, undecyl, dodecyl, —$NO_2$, —$B(R^5R^6)$, —$BF_3^-M^+$, —$R^7$—$B(R^5R^6)$, or —$R^7$—$BF_3^-M^+$, wherein R is methyl, ethyl, n-propyl, butyl, pentyl, hexyl, heptyl, octyl, nonyl, decyl, undecyl, or dodecyl.*

*23. The compound of claim 22, wherein $R^7$ is an aryl substituted with a chloride, bromide, iodide, —OH, —OC(O)R, —$OCF_3$, —C(O)R, —$CF_3$, ethyl, propyl, butyl, pentyl, hexyl, heptyl, octyl, nonyl, decyl, undecyl, dodecyl, —$NO_2$, or —$B(R^5R^6)$, wherein R is methyl, ethyl, n-propyl, butyl, pentyl, hexyl, heptyl, octyl, nonyl, decyl, undecyl, or dodecyl.*

*24. The compound of claim 17, wherein $R^4$ is an aryl substituted with a chloride, bromide, iodide, —OH, or —$B(R^5R^6)$.*

*25. The compound of claim 24, wherein $R^4$ is an aryl substituted with —$B(R^5R^6)$.*

*26. The compound of claim 22, wherein $R^4$ is phenyl substituted with —$R^7$—$B(OH)_2$.*

*27. The compound of claim 25, wherein $R^4$ is phenyl substituted with*

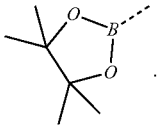

* * * * *